US008765442B2

(12) United States Patent
Grønfeldt

(10) Patent No.: US 8,765,442 B2
(45) Date of Patent: Jul. 1, 2014

(54) PROCESS FOR PRODUCTION OF AN ENZYME PRODUCT

(75) Inventor: Mette Zacho Grønfeldt, Give (DK)

(73) Assignee: DuPont Nutrition Biosciences ApS, Copenhagen (DK)

(*) Notice: Subject to any disclaimer, the term of this patent is extended or adjusted under 35 U.S.C. 154(b) by 226 days.

(21) Appl. No.: 13/140,279

(22) PCT Filed: Dec. 21, 2009

(86) PCT No.: PCT/EP2009/067690
§ 371 (c)(1),
(2), (4) Date: Sep. 29, 2011

(87) PCT Pub. No.: WO2010/070146
PCT Pub. Date: Jun. 24, 2010

(65) Prior Publication Data
US 2012/0028332 A1 Feb. 2, 2012
US 2012/0202262 A9 Aug. 9, 2012

Related U.S. Application Data

(60) Provisional application No. 61/139,493, filed on Dec. 19, 2008.

(30) Foreign Application Priority Data

Dec. 19, 2008 (EP) .................................. 08172396

(51) Int. Cl.
C12N 9/62 (2006.01)
C12N 9/98 (2006.01)
C12N 1/14 (2006.01)
A61K 38/00 (2006.01)

(52) U.S. Cl.
USPC ........... 435/225; 435/183; 435/232; 435/209; 426/14

(58) Field of Classification Search
CPC ....................................................... C12N 9/62
See application file for complete search history.

(56) References Cited

U.S. PATENT DOCUMENTS

| 3,925,160 | A | * | 12/1975 | Sanders et al. | ............... | 435/170 |
| 4,136,201 | A | * | 1/1979 | Feldman | .......... | 426/36 |
| 5,591,620 | A | | 1/1997 | Musters et al. | | |
| 2002/0037342 | A1 | * | 3/2002 | Labeille et al. | ............... | 426/61 |
| 2003/0068805 | A1 | * | 4/2003 | Madrid et al. | ............... | 435/200 |
| 2004/0191389 | A1 | * | 9/2004 | Kochhar et al. | ............... | 426/593 |
| 2013/0029384 | A1 | * | 1/2013 | Cerdobbel et al. | ............ | 435/105 |
| 2013/0089858 | A1 | * | 4/2013 | Wong et al. | ................... | 435/6.1 |

FOREIGN PATENT DOCUMENTS

| EP | 0 278 355 A2 | 8/1988 |
| EP | 0 353 188 A2 | 1/1990 |
| EP | 0 388 593 A1 | 9/1990 |
| EP | 0 421 919 A2 | 4/1991 |
| EP | 0 570 075 A2 | 11/1993 |
| EP | 1 022 329 A1 | 7/2000 |
| WO | WO 97/43423 A2 | 11/1997 |
| WO | WO 00/17367 A1 | 3/2000 |
| WO | WO 2005/021694 A1 | 3/2005 |
| WO | WO 2008/117301 A1 | 10/2008 |

OTHER PUBLICATIONS

Al-Tamimi et al. (2006) In vitro fermentation of sugar beet arabinan and arabino-oligosaccharides by the human gut microflora, J. Appl. Microbiol., vol. 1 100, pp. 407-414.*
Spagnuolo et al. (1999) Fractionation of sugar beet pulp into pectin, cellulose, and arabinose by arabinases combined with ultrafiltration, Biotech. Bioeng., vol. 64, No. 6, pp. 687-691.*
Hutnan et al. (20010 Two-step pilot-scale anaerobic treatment of sugar beet pulp, Pol. J. Environ. Stud., vol. 10, No. 4, pp. 237-243.*
Palmarola-Adrados et al. (2005) Ethanol production from non-starch carbohydrates of wheat bran, Bioresour. Technol., vol. 96, No. 7, pp. 843-850.*
Pushalkar et al. (1995) Production of beta-glucosidase by *Aspergillus terreus*, Curr. Microbiol., vol. 30, No. 5, pp. 255-258.*
Asther, M., et al., "Feruloyl esterase from *Aspergillus niger* a comparison of the production in solid state and submerged fermentation," *Process Biochemistry*, 2002, vol. 38, pp. 685-691.
Considine, A., et al., "Hydrolysis of Beet Pulp Polysaccharides by Extracts of Solid-State Cultures of *Penicillium capsulatum*," *Biotechnology and Bioengineering*, 1988, vol. 31, pp. 433-438.
De Vries, R., et al.,"aguA, the Gene Encoding an Extracellular α-Glucuronidase from *Aspergillus tubingensis*, Is Specifically Induced on Xylose and Not on Glucuronic Acid," *Journal of Bacteriology*, 1998, vol. 180(2), pp. 243-249.
De Vries, R., et al., "Synergy between enzymes from *Aspergillus* involved in the degradation of plant cell wall polysaccharides," *Carbohydrate Research*, 2000, vol. 327, pp. 401-410.
De Vries, R., et al., "*Aspergillus* Enzymes Involved in Degradation of Plant Cell Wall Polysaccharides," *Microbiology and Molecular Biology Reviews*, 2001, vol. 65(4), pp. 497-522.
De Vries, R., et al., Chapter 13, "Plant Cell Wall Degrading Enzymes Produced by *Aspergillus*," *The Mycota A Comprehensive Treatise on Fungi as Experimental Systems for Basic and Applied Research—vol. X*, edited by K. Esser and J. W. Bennett, Volume editor: H.D. Osiewacz, Springer-Verlag Berlin Heidelberg New York, 2002, pp. 263-279.
Diaz-Godinez, et al., "Expectinases produced by *Aspergillus niger* in solid-state and submerged fermentation: a comparative study," *Journal of Industrial Microbiology & Biotechnology*, 2001, vol. 26, pp. 271-275.
Grassin, C., et al., "Application of Pectinases in Beverages," *Proceedings of an International Symposium*, Wageningen, The Netherlands, 1995, pp. 453-462.
Maldonado, M., et al., "Catabolite Repression of the Synthesis of Inducible Polygalacturonase and Pectinesterase by *Aspergillus niger* sp.," *Current Microbiology*, 1989, vol. 18, pp. 303-306.
Pařenicová, J., et al., "*pgaE* encodes a fourth member of the endopolygalacturonase gene family from *Aspergillus niger*," *Eur. J Biochem.*, 1998, vol. 251, pp. 72-80.

(Continued)

Primary Examiner — Karen Cochrane Carlson
Assistant Examiner — Samuel Liu
(74) Attorney, Agent, or Firm — Alston & Bird LLP

(57) ABSTRACT

The invention relates to a process for production of an enzyme product having a plurality of enzyme activities obtained by fermentation of an *Aspergillus* strain.

24 Claims, 5 Drawing Sheets

(56) References Cited

OTHER PUBLICATIONS

Sandhya, C., et al., "Comparative evaluation of neutral protease production by *Aspergillus oryzae* in submerged and solid-state fermentation," *Process Biochemistry*, 2005, vol. 40, pp. 2689-2694.

Suykerbuyk, M., et al., "Cloning, sequence and expression of the gene coding for rhamnogalacturonase of *Aspergillus aculeatus*; a novel petinolytic enzyme," *Appl. Microbiol Biotechnol*, 1995, vol. 43, pp. 861-870.

* cited by examiner

PROCESS FOR PRODUCTION OF AN ENZYME PRODUCT

CROSS-REFERENCE TO RELATED APPLICATIONS

This application is the U.S. National Stage of International Application PCT/EP2009/067690 filed Dec. 21, 2009, which designates the U.S and was published by the International Bureau in English on Jun. 24, 2010, and which claims the benefit of European Patent Application No. 08172396.7, filed Dec. 19, 2008, and U.S. Provisional Application No. 61/139,493, filed Dec. 19, 2008, all of which are hereby incorporated herein in their entirety by reference.

FIELD OF THE INVENTION

The invention relates to a process of producing an enzyme product having a plurality of enzyme activities by submerged fermentation with *Aspergillus*.

BACKGROUND OF THE INVENTION

Enzymes are widely used in the food and feed industries such as in the fruit and vegetable processing industry.

In recent years, using enzymes to process fruit (including berry) mash has become state-of-the-art in juice e.g. citrus, apple and pear production as highest possible yields and throughput have become paramount. Pectin, a natural substance found in all fruit acts as cell glue, giving structure to the fruit. In fruit mashes, pectin binds with water to increase the viscosity and makes it difficult to release the juice in the liquid/solid separation by presses or decanters. The use of enzymes allows producers to control production according to demand.

In citrus fruit processing, the application of enzymes reduces juice viscosity, eliminating the risk of jellification during fruit juice concentration and storage and securing high cloud stability. Applied during the pulp extraction process, enzymes facilitate the release of juice and solids, increasing yield and improving cost efficiency. A stable cloud—or, in the case of lemon juice, successful clarification—is an important measure of the final product's superior quality. Essential citrus oils can also be recovered while using enzymes in citrus fruit processing. Apart from providing access to a valuable commodity, citrus oil recovery is important from a sustainability point of view, ensuring a low content of the bactericidal oils in wastewater for improved wastewater biodegradability and reducing overall water consumption. Enzymes are also used in the production of high clarity apple and pear juice which is dependent on the complete breakdown of starch and pectin content. This has been achieved by the addition of pectinases and starch-degrading enzymes to the juice before clarification and filtration. Added to the fruit mash before pressing and juice separation, pectinases lead to a reduction in mash viscosity, resulting in increased juice yield and optimised processing capacity. Less waste pomace and easier cleaning of fruit presses are other value-adding advantages. Also in wine production enzymes are used for transferring valuable components, such as aromas, colour and tannins, from the grape to the wine. Enzymes can furthermore help to preserve wine quality, sometimes over many years in storage. They also reduce fermentation time and promote clarification, filtration and stabilisation.

As mentioned above enzyme preparations are often used during fruit juice manufacture in the steps of extraction and liquefaction of fruit and fruit juice clarification. The commercial enzyme preparations contain a mixture of mainly pectinases (e.g. polygalacturonases, pectin esterases, pectin lyases) together with minor quantities of other hydrolytic enzymes such as arabinanases, galactanases and xylanases. The substrates for the various pectinases are pectins, which are polygalacturonides of high molecular weight (20-100 kDalton) consisting of alpha-1,4-glycosidic bound D-galacturonic acid polymers. Some of the uronic acid groups are esterified with methanol. The polygalacturonic backbone is interrupted by so-called hairy regions, consisting of a rhamnose-galacturonic acid backbone with arabinose-rich side chains.

The pectin degrading enzymes like polygalacturonase, pectin methyl esterase, pectin lyase or pectate lyase are important, especially in fruit and vegetable processing such as fruit juice processing or wine making, where their ability to catalyse the degradation of the backbone of the pectin polymer is utilized.

Pectins occur in nature as constituents of higher plant cell walls. They are found in the primary cell wall and middle lamella where they are embedded in cellulose fibrils. The composition of pectin and the degree of methylation is variable among plant species and moreover dependent on the age and maturity of the fruit. Among the richest sources of pectins are lemon and orange rind, which can contain up to 30% of this polysaccharide. Pectinases can degrade the carbohydrate polymer either by hydrolysis of the alpha-1,4-glycosidic bond (endo and exopolygalacturonases) or by transelimination reaction (pectin lyases). Pectin esterases can demethylate highly esterified pectin into polygalacturonic acid. Pectin lyases are specific for highly esterified pectins, polygalacturonases hydrolyse low esterified pectins. Consequently highly esterified pectins can be degraded by pectin lyases or the combination of pectin esterases and polygalacturonases.

In the various stages of fruit and vegetable processing pectinases play an important role. Originally pectinases were used for treatment of soft fruit to ensure high yields of juice and pigments upon pressing and to clarify raw press juices. Polygalacturonases are used as macerating enzymes for the production of pulpy nectars, loose cell suspensions that are the result of limited pectin breakdown particularly in the middle lamella. A combination of several pectinases together with cellulolytic enzymes is needed to almost completely liquefy fruit tissue, thereby facilitating extraction. The clarification of apple juices can for example be improved by the combined activity of pectin esterases and polygalacturonases or by pectin lyases for which the highly esterified apple pectin is an ideal substrate.

Most of the pectinases present in commercial preparations are of fungal origin. *Aspergillus niger* (*A. niger*) is a very important organism for the industrial production of pectin degrading enzymes. In *A. niger* the various pectinases are not expressed constitutively. Pectin or degradation products of the pectin molecule are needed as inducing substances. The fermentation conditions for pectinase production often result in a wide spectrum of pectinases. Moreover, *A. niger* produces many isoenzymes of the various pectinases. Several patents have published describing that genes encoding polygalacturonase (EP 421 919, EP 0 388 593), pectin lyases (EP 0 278 355, EP 0 353 188) and pectin esterases (EP 0 388 593) have been isolated and used for the construction of overproducing transformants. These transformants allow the production of specific enzymes, needed e.g. in maceration applications and in studies on the effect of the various pectinases in processes like liquefaction and clarification.

The isolation and characterization of a cell-wall polysaccharide from apple juice obtained after the liquefaction process in which the juice was released from the apple pulp by the combined action of pectolytic and cellulolytic enzymes has also been described. These cell-wall polysaccharides resemble the hairy regions of apple pectin (a rhamnose-galacturonic acid backbone with arabinose rich side chains) and have been called Modified Hairy Regions (MHR). Hairy regions are known to be present not only in apples but also in carrots, grapes and strawberries and are probably a common part of pectin molecules. The modified hairy regions are resistant to breakdown by the enzymes present in most pure and technical pectinase and cellulase preparations. A commercial crude enzyme preparation obtained from *Aspergillus aculeatus* has been found to be able to depolymerize the rhamnogalacturon backbone of these fragments. This activity was made visible by measuring the shift in molecular weight distribution using High Performance Gel Permeation Chromatography (HPGPC). The enzyme responsible for the degradation of the modified hairy regions prepared from apple juice are called rhamnogalacturonase (RGase). The enzyme can split glycosidic linkages in the rhamnogalacturonan backbone of (apple) pectins producing, besides other not yet fully identified reaction products, a range of oligomers composed of galacturonic acid, rhamnose and galactose with rhamnose at the non reducing end, hence the name rhamnogalacturonase (RG-ase) for this novel enzyme.

U.S. Pat. No. 5,591,620 describe the isolation of an *Aspergillus* gene encoding rhamnogalacturonase (RG-ase) and the construction of recombinant *Aspergillus* strains with overexpression of RG-ase. These strains can be used for the commercial production of RG-ase.

EP 1658359 describes a preparation comprising a mass consisting of olives or olive constituents and an enzymatic mixture containing at least one pectinesterase, at least one endopolygalacturonase and at least one exopolygalacturonase. In said preparation the ratio of the pectinesterase activity to the endopolygalacturonase activity is at least 0.13 and the ratio of the pectinesterase activity to the exopolygalacturonase activity is at least 0.3.

WO2008/117301 relates to a process for the production of a multienzyme system by fermentation. WO2008/117301 also describes the use of *Aspergillus oryzae* MTCC 5154 under optimized conditions for the production of a multienzyme system by submerged fermentation. The product described is a mixture of different enzymes such as α-amylase, amyloglucosidase, carboxy methyl cellulase, pectinase, beta-galactosidase and xylanase.

In "*Aspergillus* Enzymes Involved in Degradation of Plant Cell Wall Polysaccharies", Microbiology and Molecular Biology Reviews, December 2001, p. 497-522 de Vries et al describes different classes of enzymes involved in plant cell wall polysaccharide degradation produced by *Aspergilli*, the genes encoding these enzymes, and the regulation of these genes. The cell wall degrading activities that have been detected from *Aspergillus* strains are furthermore described.

WO097/43423 describes purification of an α-glucuronidase from a crude, mixed enzyme preparation Pektinase 146, which is marketed as a pectinase source derived from an *Aspergillus* strain having the reference number 4M146.

Commercial preparations containing a number of different degrading enzymes are also available.

However, as highest possible yields and throughput are increasingly important in industrial processes more efficient processes providing enzymatic solutions are still needed.

SUMMARY OF THE INVENTION

In one aspect, a process for the production of an enzyme product, the process comprising the steps of submerged fermentation of an *Aspergillus* strain in a fermentation medium which medium comprises vegetable material comprising pectin and arabinan to obtain a fermentation broth, and optionally recovery of the enzyme product in the form of a cell free broth from said fermentation broth, and the enzyme product obtained by the process, is provided.

In one aspect, an enzyme product comprising at least the following enzyme activities:
endo-polygalacturonase activity,
exo-polygalacturonase activity,
pectinesterase activity,
pectin lyase activity,
cellulase activity,
xylanase activity and
arabinanase activity
and where said enzyme product is an expression product obtained by submerged fermentation of an *Aspergillus* strain, is provided.

In one aspect, a process for the production of an enzyme product, the process comprising the steps of submerged fermentation of an *Aspergillus tubingensis* strain in a fermentation medium to obtain a fermentation broth, and optionally recovery of the enzyme product in the form of a cell free broth from said fermentation broth, and the enzyme product obtained by the process, is provided. In one aspect, the fermentation medium comprises vegetable material which comprises pectin and arabinan.

In one aspect, an enzyme product preparation comprising the enzyme product according to the invention, an enzyme carrier and optionally a stabilizer and/or a preservative, is provided.

In one aspect, an enzyme product obtainable by a process according to the invention, is provided.

In one aspect, *Aspergillus tubingensis* having the deposit accession number CBS123488 or a derivative or progeny thereof, is provided.

In one aspect, an isolated *Aspergillus tubingensis* having the deposit accession number CBS123488 or a derivative or progeny thereof, is provided.

In one aspect, a fungal culture having characteristics substantially identical to that of the strain *Aspergillus tubingensis* having the deposit accession number CBS123488, is provided.

In a further aspect, a fermentation medium for submerged fermentation of an *Aspergillus* strain, which medium comprises sugar beet pulp and wheat bran, is provided.

DETAILED DESCRIPTION OF THE INVENTION

Figure 1:
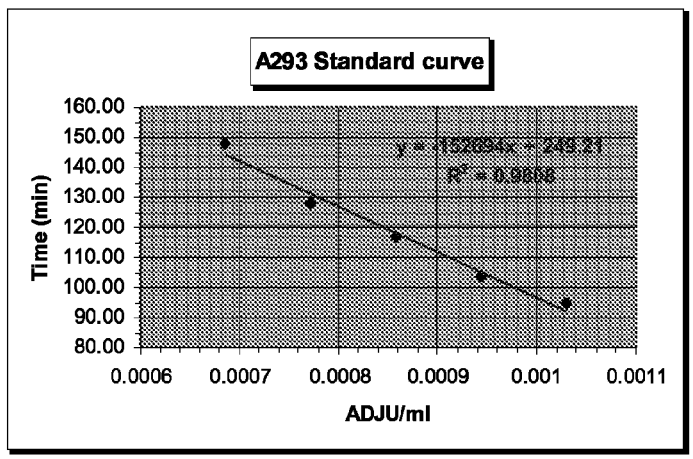
FIG. 1 shows an AJDU standard curve made as described in "Assay 2" in the following under the heading "Assays".

In one aspect, a process for the production of an enzyme product, the process comprising the steps of submerged fermentation of an *Aspergillus* strain in a fermentation medium which medium comprises vegetable material comprising pectin and arabinan to obtain a fermentation broth, and optionally recovery of the enzyme product in the form of a cell free broth from said fermentation broth, is provided. In a further aspect, a process for the production of an enzyme product, the process comprising the steps of submerged fermentation of an *Aspergillus* strain in a fermentation medium which medium comprises vegetable material comprising pectin and arabinan to obtain a fermentation broth, and recovery of the enzyme product in the form of a cell free broth from said fermentation broth, is provided. In yet a further aspect, a process for the production of an enzyme product, the process comprising the steps of submerged fermentation of an *Aspergillus* strain in a fermentation medium which medium comprises sugar beet pulp and wheat bran to obtain a fermentation broth, and recovery of the enzyme product in the form of a cell free broth from said fermentation broth, is provided.

In one aspect, a process for the production of an enzyme product, the process comprising the steps of submerged fermentation of an *Aspergillus tubingensis* strain in a fermentation medium to obtain a fermentation broth, and optionally recovery of the enzyme product in the form of a cell free broth from said fermentation broth, and the enzyme product obtained by the process, is provided. In a further aspect, a process for the production of an enzyme product, the process comprising the steps of submerged fermentation of an *Aspergillus tubingensis* strain in a fermentation medium to obtain a fermentation broth, and recovery of the enzyme product in the form of a cell free broth from said fermentation broth, is provided. In yet a further aspect, a process for the production of an enzyme product, the process comprising the steps of submerged fermentation of an *Aspergillus tubingensis* strain in a fermentation medium which comprises vegetable material comprising pectin and arabinan to obtain a fermentation broth, and recovery of the enzyme product in the form of a cell free broth from said fermentation broth, is provided.

The vegetable material comprising pectin and arabinan to be used may be any vegetable material comprising pectin and arabinan, such as sugar beet pulp or cereal bran or a combination thereof.

In a further aspect, the vegetable material comprises sugar beet pulp. In a further aspect, the vegetable material comprises cereal bran such as wheat bran. In yet a further aspect a mixture of cereal bran such as wheat bran and sugar beet pulp is used as the vegetable material.

Without wanting to be bound by any theory it is believed that the vegetable material comprising pectin and arabinan, such as wheat brand and/or sugar beet pulp have an impact on the composition of the enzyme product produced. It is further believed that the arabinan content of the vegetable material such as in wheat brand and/or sugar beet pulp relates directly or indirectly to the relatively high arabinanase content of the enzyme product obtained. Such a high arabinanase content, among other enzyme activities, is believed to be important for the applications of the enzyme product in e.g. the fruit-related and/or wine applications of the enzyme product.

In one aspect, the vegetable material comprises sugar beet pulp. In a further aspect, the fermentation medium comprises sugar beet pulp in the range of 1-30% w/w, such as sugar beet pulp in the range of 2-8% w/w, or such as sugar beet pulp in the range of 3-7% w/w. In a further aspect, the sugar beet pulp has a sugar content of 0.5-20% w/w, or such as a sugar content of 2-8% w/w. In a further aspect, the sugar beet pulp has an arabinan content of 5-40% w/w. It has been found that an especially useful type of sugar beet pulp is un-molassed sugar beet pulp.

In one aspect, the vegetable material comprises cereal bran. In a further aspect, the vegetable material is a mixture of cereal bran and sugar beet pulp. In yet a further aspect, the cereal bran is wheat bran. In a further aspect, the wheat bran has an arabinan content of 2-20% w/w. The term "fermentation" means in the present context production of substances such as enzymes by growing a microorganism(s) in a fermentation medium/culture.

In one aspect, the *Aspergillus* strain is fermented as one single culture of an *Aspergillus* strain. In a further aspect, the *Aspergillus* culture is one single culture of an *Aspergillus tubingensis* strain. In yet a further aspect, the *Aspergillus* strain such as the *Aspergillus tubingensis* strain has not been genetically modified (non-GMO). In yet a further aspect, the *Aspergillus* strain such as the *Aspergilus tubingensis* strain has not been self-cloned. In one aspect, the *Aspergillus tubingensis* strain has the deposit accession number CBS123488. In yet a further aspect, the *Aspergillus* strain such as the *Aspergillus tubingensis* strain has been genetically modified (GMO).

In one aspect, the pH during the fermentation is in the range of 2.7-6.5. In one aspect, the pH during the fermentation is in the range of 3-4.5. In a further aspect, the pH during the fermentation is in the range of 3-4. In yet a further aspect, the pH during the fermentation is in the range of 3.2-3.7. In yet a further aspect, the pH during the fermentation is in the range of 3.3-3.7. The pH profile may be kept constant or may vary during fermentation within the stated ranges. In one aspect, the pH during the fermentation is kept such that the pH at the most varies within a pH-range of ±1, such as within a pH-range of ±0.8, such as within a pH-range of ±0.6, or such as within a pH-range of ±0.5, such as within a pH-range of ±0.3, such as within a pH-range of ±0.25, such as such as within a pH-range of ±0.2, such as within a pH-range of ±0.15, such as within a pH-range of ±0.1, such as within a pH-range of ±0.05. In one aspect, the start pH is e.g. 7.0, 6.5, 6.0, 5.5, or 5.0 and the end pH is at e.g. 4.5, 4.0, 3.5 or 3.0.

It is known in the art that the pH-1 may vary at different locations in the fermenter/bioreactor. Furthermore, these pH variations may depend on the viscosity of the medium/broth, which is generally more viscous in the beginning than towards the end of the fermentation.

In one aspect, the temperature during the fermentation is in the range of 25-40° C. In a further aspect, the temperature during the fermentation is in the range of 28-34° C. The temperature profile may be kept constant or varied during fermentation within the stated intervals.

In yet a further aspect, the fermentation is conducted as an aerobic fermentation.

In one aspect, the fermentation medium further comprises ammonium sulphate and/or potassium nitrate.

In one aspect, an enzyme product comprising at least the following enzyme activities:
  i. endo-polygalacturonase activity
  ii. exo-polygalacturonase activity iii. pectinesterase activity
iv. pectin lyase activity
v. 1,3-β-glucanase activity (or cellulase or laminarinase or any combination therof)
vi. xylanase activity,
vii. arabinanase activity and
viii. optionally arabinofuranosidase activity and where said enzyme product is an expression product obtained by submerged fermentation of an *Aspergillus* strain, is provided.

In one aspect according to the invention, the enzyme product is in the form of a cell free broth from a fermentation broth. In a variant of this aspect, the enzyme product is present in a fermentation broth.

In one aspect, an enzyme product comprising at least the following enzyme activities:
i. endo-polygalacturonase activity
ii. exo-polygalacturonase activity
iii. pectinesterase activity
iv. pectin lyase activity
v. cellulase activity
vi. xylanase activity and
vii. arabinanase activity and
viii. optionally arabinofuranosidase.

and where said enzyme product is an expression product obtained by submerged fermentation of an *Aspergillus* strain, is provided. In a further aspect, the *Aspergillus* strain is a single culture.

In one aspect, the enzyme product further comprises one or more activities selected from the group consisting of rhamnogalacturonase activity, hemicellulase activity, glucoamylase activity, holoamylase activity and laminarinase activity, is provided.

In a further aspect, the enzyme product further comprises rhamnogalacturonase activity. In a further aspect, the enzyme product further comprises hemicellulases activity. In a further aspect, the enzyme product further comprises glucoamylase activity. In a further aspect, the enzyme product further comprises holoamylase activity. In a further aspect, the enzyme product further comprises laminarinase activity such as 1,3-β-glucanase. In a further aspect, the enzyme product further comprises amylase activity.

The enzyme product may also comprise hemicellulolytic activity.

In a further aspect, said enzyme product is an expression product obtained by submerged fermentation of one single culture of an *Aspergillus* strain.

In a further aspect, an enzyme product comprising at least the following enzymes
i. an endo-polygalacturonase classified in EC 3.2.1.15
ii. an exo-polygalacturonase classified in EC 3.2.1.67
iii. a pectinesterase classified in EC 3.1.1.11
iv. a pectin lyase classified in EC 4.2.2.10
v. a cellulase classified in EC 3.2.1.4
vi. a xylanase classified in EC 3.2.1.8 and
vii. an arabinanase classified in EC 3.2.1.99, and
viii. optionally an arabinofuranosidase classified in EC 3.2.1.55.

and where said enzyme product is an expression product obtained by submerged fermentation of an *Aspergillus* strain, is provided.

In one aspect, the enzyme product has a higher exo-polygalacturonase activity when prepared by submerged fermentation compared to the exo-polygalacturonase activity in an enzyme product prepared by surface fermentation of the same culture and using a comparable fermentation medium comprising cereal/wheat bran and sugar beet pulp pellets, such as 1.2, 1.3, 1.4, 1.5, 1.6, 1.7, 1.8, 1.9 or 2.0 times higher by submerged fermentation compared to surface fermentation as measured by Assay 5. In another aspect, the enzyme product has a higher total enzymatic activity as measured by Assay 1 when prepared by submerged fermentation compared to the total enzymatic activity as measured by Assay 1 in an enzyme product prepared by surface fermentation of the same culture and using a comparable fermentation medium comprising cereal/wheat bran and sugar beet pulp pellets, such as 1.2, 1.3, 1.4, 1.5, 1.6, or 1.7 times higher by submerged fermentation compared to surface fermentation.

In some embodiments herein advantages including but not limited to one or more of higher yield, improved process control, improved pH control (not depending on buffer and/or buffer capacity), improved aeration, improved sterility, reduction of growth of undesired microorganisms/contaminants, reduction of undesired reactions during media preparation, such as Maillard reaction(s), i.e. chemical reaction between amino acids and reducing sugar upon heating, is provided by the present processes and/or products.

In some embodiments herein a further advantage of the current invention is that the enzymatic activities are present in the liquid/aqueous/dissolved portion of the fermentation broth—in contrast to surface fermentation, where the solid medium has to be extracted with an appropriate buffer in order to harvest the enzymes/enzymatic activities.

In one aspect, the enzyme product provided herein by submerged fermentation has one or more higher enzyme activities, such as one or more activity selected from the group consisting of endo-polygalacturonase activity, exo-polygalacturonase activity, pectinesterase activity, pectin lyase activity, 1,3-β-glucanase/cellulase/laminarase activity, xylanase activity, arabinanase activity, arabinofuranosidase activity, rhannnogalacturonase activity, glucoamylase activity, amylase activity, holoamylase activity, arabinofuranosidase activity, QVC Viscometric activity according to assay 1, Apple Juice Depectinization Units according to assay 2, and/or Pectin transeliminase activity according to assay 3.

Without wishing to be bound by any theory, it is believed that one or more enzyme activities, selected from the group consisting of endo-polygalacturonase activity, exo-polygalacturonase activity, pectinesterase activity, pectin lyase activity, 1,3-β-glucanase activity, cellulase activity, laminarase activity, xylanase activity, arabinanase activity, arabinofuranosidase activity, rhamnogalacturonase activity, glucoamylase activity, amylase activity, holoamylase activity, arabinofuranosidase activity, shows linear or approximately linear correlation to one or more of: QVC Viscometric activity determination measured according to assay 1, Apple Juice Depectinization Units activity according to assay 2 and/or Pectin transeliminase activity/Pectin Lyase activity according to assay 3. In one aspect, the pectin lyase activity/pectin transeliminase activity as described in "Assay 3" is used for correlating or predicting the enzymatic activity of the present enzyme product or the present enzyme preparation.

In a further aspect, said enzyme product is an expression product obtained by submerged fermentation of an *Aspergillus* strain such as one single culture of an *Aspergillus* strain. In one aspect, the medium used for said submerged fermentation comprises sugar beet pulp. In one aspect, the medium used for said submerged fermentation comprises cereal bran, such as wheat bran. In one aspect, the medium used for the submerged fermentation comprises sugar beet pulp in the range of 1-30% (w/w).

In one aspect of the invention, the enzyme product comprises
i. one or more endo-polygalacturonase(s),
ii. one or more exo-polygalacturonase(s), iii. one or more pectinesterase(s),
iv. one or more pectin lyase(s),
v. one or more laminarinase(s),
vi. one or more xylanase(s),
vii. one or more arabinanase(s) and
viii. optionally one or more arabinofuranosidase(s).

In one aspect of the invention, the enzyme product comprises
i. one or more endo-polygalacturonase(s),
ii. one or more exo-polygalacturonase(s),
iii. one or more pectinesterase(s),
iv. one or more pectin lyase(s),
v. one or more cellulose(s),
vi. one or more xylanase(s),
vii. one or more arabinanase(s) and
viii. optionally one or more arabinofuranosidase(s).

In a further aspect, the enzyme product further comprises a rhamnogalacturonase.

In a further aspect, the enzyme product further comprises one or more hemicellulases such as feruloyl esterase classified in EC 3.1.1.73.

In yet a further aspect, the enzyme product comprises one or more amylase(s) classified in EC 3.2.1.1, EC 3.2.1.2, EC 3.2.1.3, EC 3.2.1.20, EC 3.2.1.60, EC 3.2.1.68, EC 3.2.1.98 or EC 3.2.1.133.

In yet a further aspect, the enzyme product comprises one or more glucoannylase(s) classified in EC 3.2.1.3 or EC 3.2.1.20.

In yet a further aspect, the enzyme product comprises one or more holoamylase(s) classified in EC 3.2.1.133.

In one aspect of the invention, the enzyme product according to the invention comprises at least the following enzymes:
i. one or more endo-polygalacturonase(s),
ii. one or more exo-polygalacturonase(s),
iii. one or more pectinesterase(s),
iv. one or more pectin lyase(s),
v. one or more cellulase(s),
vi. one or more xylanase(s),
vii. one or more arabinanase(s)
viii. one or more rhamnogalacturonase(s)
ix. one or more glucoamylase(s)
x. one or more amylase(s)
xi. one or more holoamylase(s) and
xii. optionally one or more arabinofuranosidase(s).

In one aspect of the invention, endo-polygalacturonase activity is determined as described in "Assay 6". In a further aspect of the invention, exo-polygalacturonase activity is determined as described in "Assay 5". In a further aspect of the invention, pectinesterase activity is determined as described in "Assay 7". In a further aspect of the invention, pectin lyase activity is determined as described in "Assay 3". In a further aspect of the invention, arabinanase activity is determined as described in "Assay 8". In a further aspect of the invention, cellulase activity is determined as described in "Assay 9". In a further aspect of the invention, xylanase activity is determined as described in "Assay 11".

As described above the enzyme product according to the invention may also comprise one or more further activities. In one aspect of the invention, amylase activity is determined as described in "Assay 12". In one aspect of the invention, glucoamylase activity is determined as described in "Assay 14". In one aspect of the invention, holoamylase activity is determined as described in "Assay 13". In a further aspect of the invention, laminarinase activity is determined as described in "Assay 10".

In a further aspect, an enzyme product having the following enzymatic activities e.g. measured as described in the following assays described under the heading "Assays": endo-polygalacturonase activity and having at least the following activities exo-polygalacturonase activity, pectinesterase activity, pectin lyase activity, arabinanase activity, cellulase activity, and xylanase activity, and where said enzyme product is a natural expression product obtained by submerged fermentation of one single culture of the strain Aspergillus, is provided.

The term "enzyme complex" used interchangeably with the term "enzyme product" herein means in the present context a product or complex comprising a mixture of several enzymes having different enzymatic activity and/or classified under different Enzyme Commission numbers (EC number). In a further aspect, the enzyme complex also comprises side activities. In one aspect, the "enzyme complex" or "enzyme product" is a substantially cell-free fermentation broth obtained by submerged fermentation, optionally concentrated. In a further aspect, the "enzyme complex" or "enzyme product" is still present in the fermentation broth comprising cells obtained by submerged fermentation.

The term "side-activity" refers in the present context to the one or more additional activities an enzyme may have on other substrates which is not its main substrate or it refers to other activities an enzyme product may have other than its main activity.

The term "different enzymes" or "enzymes having different enzymatic activity" refers to enzymes having different substrate specificity as determined by standard methods know to persons skilled in the art or wherein the enzymes has the same enzyme substrate specificity but differs on the typical enzymes parameters like pH optimum, temperature optimum, Km or Ip (isoelectric point) as measured by conventional methods.

Thus, in one aspect two or more enzymatic activities can be the result of one, or more enzyme(s) possessing one or more side-activities.

The enzyme product according to the invention is preferably expressed by a single culture by multi-expression.

In one aspect, the enzyme product is thus obtainable by fermentation of a single culture, wherein the single culture refers to a culture grown from one organism. A culture according to the invention is preferably substantially pure, such as at least 90% by weight pure, preferably at least 95% by weight pure, more preferably at least 97% by weight pure, even more preferably at least 99% by weight pure. It is to be understood that "a substantially pure culture" could contain smaller amounts of other organisms such as other clones of the same strain or other strains.

Pectin is very complex and it has been found that an enzyme product according to the present invention comprising various enzymes with different activities is very suitable for degradation thereof.

In one aspect of the invention, the enzyme product according to the invention comprises sufficient side activities to degrade non-pectin poly-saccharide compounds such as e.g. measured by "Assay 1" or "Assay 2" described under the heading "Assays".

In a further aspect of the invention, the enzyme product according to the invention contains the side-activities necessary to degrade the very complex non-pectin polysaccharide compounds as determined by "Assay 1".

In one aspect of the invention, the enzyme product according to the invention comprises at least 10 different side-activities.

In one aspect of the invention, the enzyme product according to the invention comprises at least 15 different side-activities.

In one aspect of the invention, the enzyme product according to the invention comprises at least 20 different side-activities.

In one aspect of the invention, the enzyme product according to the invention comprises at least 60 different side-activities.

Endo-polygalacturonase is classified in EC 3.2.1.15 and catalyse a random hydrolysis of (1→4)-alpha-D-galactosiduronic linkages in pectate and other galacturonans.

A number of different enzymes belong to this classification including D-galacturonase, endo-D-galacturonanase, endo-D-galacturonase, endopolygalacturonate lyase.

Endo-polygalacturonase (EC 3.2.1.15) hydrolyses the (internal) glycosidic linkages in the polygalacturonic acid chain, forming oligogalacturonic acid fragments.

"Polygalacturonase activity" refers to the ability to hydrolyse glycosidic linkages in polygalacturonic acid chains.

Endo-polygalacturonase (EC. 3.2.1.15) activity refers to the ability to hydrolyse internal glycosidic linkages in a polygalacturonic acid chain, as opposed to exo-polygalacturonase (EC. 3.2.1.67) activity which refers to the ability to release terminal polygalacturonic acid from a polygalacturonic acid chain by hydrolysis of the (terminal) glycosidic linkage.

Exo-polygalacturonase activity may be determined as described below, whereby 1 unit of exo-polygalacturonase activity is defined as the amount of enzyme capable of releasing 1 mole of reducing sugar ends per minute from polygalacturonic acid (Sigma) as the model substrate at 30 deg. C in 50 mM sodium acetate buffer, pH 4.2, with 0.25% (w/v) substrate concentration.

Endo-polygalacturonase activity may be determined qualitatively by spotting a droplet of culture medium on agar plates containing 0.1% (w/v) polygalacturonic acid, pH 4 (Sigma, P3850). After incubation at 30 deg. C for at least 30 min, the plate was flooded with 4 M HCl. Endo-polygalacturonase activity was visualized as a white halo in a turbid background. Alternatively, the plates were stained by incubation with a 0.02% (w/v) ruthenium red solution. In that case, endo-polygalacturonase activity showed as a white spot in a red background.

The catalytic activity of exo-polygalacturonase was determined quantitatively by means of colorimetric detection of reducing sugar release as described previously (by Parenicova et al., in Eur. J. biochem. 251, 72-80, 1998 entitled "pgaE encodes a fourth member of the endopolygalacturonase gene family from *Aspergillus niger*"). The hydrolysis reactions were carried out at 30 deg. C in 50 mM sodium acetate buffer, pH 4.2, with 0.25% (w/v) polygalacturonic acid (Sigma) as the model substrate. Enzyme activity is expressed in U/mg were 1 unit corresponds to 1 mole of reducing ends liberated per minute.

In one aspect of the invention, the endo-polygalacturonase activity of the product is measured by "Assay 6" as described in the following under the heading "Assays". This method measures the physical effect of the activity upon polygalactuonase i.e reduction in viscosity. This method is specific for endo-activity as any exo-activity (production of sugars) will have little or no effect upon viscosity.

In another aspect of the invention, the exo-polygalacturonase activity of the product is measured by "Assay 5" as described in the following under the heading "Assays". This method measures reducing groups and thus an exo-activity.

In one aspect, the enzyme product has a higher endo-polygalacturonase activity than exo-polygalacturonase activity. In a further aspect of the invention, the enzyme product has a ratio between exo- and endo-polygalacturonase activity of 1:1 and 8:1, such as between 2:1 to 6:1, such as between 3:1 to 6:1. The ratio may be determined by measuring the activity of exo-polygalacturonase in "Assay 5" and endo-polygalacturonase activity in "Assay 6".

As described in "Assay 6" one unit of endo-polygalacturonase activity is defined as the amount of enzyme which will hydrolyse the substrate, reducing the viscosity of the solution, to give a change in relative fluidity of 1 dimensionless unit per minute under the conditions of the assay (pH 3.5 and 30° C.).

As described in "Assay 5" one unit of exo-polygalacturonase activity is defined as the amount of enzyme which produces 1 μmole D-galacturonic acid equivalents per minute under the conditions of the assay (pH 3.5 and 50° C.).

In one aspect, the ratio between exo- and endo-polygalacturonase is at least about 1:1, at least 2:1 or at least 3:1 as defined by the units determination by the method of "Assay 5" as compared to the method of "Assay 6".

In a further aspect, the enzyme product according to the invention has pectinesterase activity. In one aspect of the invention, the pectinesterase activity of the product is measured by a reaction, catalysed by pectinesterase, involving the de-esterification of methyl-esterified D-galactosiduronic acid units in pectic compounds (e.g. homogalacturonan) giving acidic pectins and methanol, the acid pectins are then substrates for pectin depolymerising enzymes.

Pectinesterase (pectin methyl esterase) is classified in EC 3.1.1.11 and catalyse the reaction:

Pectin+$n$H20<=>$n$ methanol+pectate

Pectin esterase is also named pectin demethoxylase, pectin methoxylase and pectin methylesterase.

In one aspect of the invention, the pectinesterase activity of the product is measured in "Assay 7" as described in the following under the heading "Assays".

One unit of pectinesterase activity is defined as the amount of enzyme that catalyses the hydrolysis of 1 μmole of methyl ester bonds (releasing 1 μmole pectic acid) per minute under the conditions of "Assay 7" (pH 4.6 and 30° C.) or other specified pH and temperature levels.

In a further aspect, the enzyme product according to the invention has pectin lyase activity

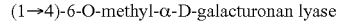
(1→4)-6-O-methyl-α-D-galacturonan lyase

Pectin lyase is also named pectin transeliminase, endopectin lyase, pectinmethyltranseliminase, pectolyase or polymethylgalacturonic transeliminase.

Pectin lyase (pectin transeliminase) is classified as EC 4.2.2.10. This enzyme catalyse the cleavage of (1→4)-alpha-D-galacturonan methyl ester to give oligosaccharides with 4-deoxy-6-O-methyl-alpha-D-galact-4-enuronosyl groups at their non-reducing ends.

In one aspect of the invention, the pectin lyase activity of the enzyme product according to the invention is measured by the generation of 4,5-unsaturated oligogalacturonates caused by a random cleavage of internal α-1,4 bonds between galacturonic acid residues of pectin.

Pectin lyase activity can be determined by the enzymatic hydrolysis of internal α-1,4 bonds between galacturonic acid residues in an apple pectin substrate such as e.g. described in "Assay 3" in the following under the heading "Assays". The progress of the reaction (characterised by the increase in 4,5-unsaturated oligogalacturonates) is followed by an increase in absorbance (due to the formation of unsaturated bonds) using a spectrophotometer. Enzyme activity is calculated from the increase in absorbance at 238 nm per unit time.

The assay can be carried out at pH 3.5 and 30° C., or it can be performed at different pH and temperature values for the additional characterisation and specification of enzymes.

One unit of pectin lyase activity is defined as the amount of enzyme (normalised for total assay volume) that gives an increase in $\Delta OD_{238\ nm} \cdot min^{-1}$ under the conditions of the assay (pH 3.5 and 30° C.).

In one aspect, the enzyme product according to the invention has arabinanase activity. The term "arabinase" and the term "arabinanase" have been used interchangeably herein and both describes arabinanase as classified in EC 3.2.1.99. The systematic name is 5-α-L-arabinan 5-α-L-arabinanohydrolase but it has several other names such as arabinan endo-1,5-α-L-arabinosidase, and endo-1,5-α-L-arabinanase, endo-α-1,5-arabanase, endo-arabanase, 1,5-α-L-arabinan and 1,5-α-L-arabinanohydrolase. Arabinase endohydrolyse (1→5)-α-arabinofuranosidic linkages in (1→5)-arabinans. Arabinanase also acts on arabinan.

In one aspect of the invention, the arabinanase activity (or arabinase activity) of the enzyme product according to the invention is measured by "Assay 8" as described in the following under the heading "Assays". The assay can be carried out at pH 3.5 and 50° C. using sugar beet arabinan as substrate, and it can be performed at different pH and temperature values for the additional characterisation and specification of enzymes. Enzyme activity is calculated from the increase in absorbance at 540 nm per unit time.

One unit of arabinanase activity is defined as the amount of enzyme (normalised for total assay volume) that gives an increase in $\Delta OD_{540\ nm} \cdot min^{-1}$ under the conditions of the assay (pH 3.5 and 50° C.).

In one aspect, the enzyme product according to the invention has arabinofuranosidase activity. The term "arabinofuranosidase" describes arabinofuranosidase as classified in EC 3.2.1.55. The systematic name is Alpha-N-arabinofuranosidase. Other names are alpha-L-arabinofuranosidase, arabinofuranosidase and arabinosidase.

The arabinofuranosidase acts on α-L-arabinofuranosides, α-L-arabinans containing (1,3)- and/or (1,5)-linkages, arabinoxylans and arabinogalactans.

In one aspect of the invention, the arabinofuranosidase activity of the enzyme product according to the invention is measured by "Assay 16" as described in the following under the heading "Assays". The assay can be carried out at pH 5.0 and 50° C. using p-nitrophenyl α-L-arabinofuranoside, and it can be performed at different pH and temperature values for the additional characterisation and specification of enzymes. A product of the reaction, p-nitrophenol is determined colourimetrically (after pH adjustment). Enzyme activity is calculated from the relationship between the concentration of p-nitrophenol and absorbance at 400 nm.

One unit of α-N-arabinofuranosidase activity is defined as the amount of enzyme which produces 1 μmole p-nitrophenol from p-nitrophenyl α-L-arabinofuranoside per minute under the conditions of the assay (pH 5.0 and 50° C. (or as specified)).

In one aspect, the enzyme product according to the invention has cellulolytic activity. The systematic name of cellulose is 4-(1,3;1,4)-β-D-glucan 4-glucanohydrolase and cellulolytic enzymes or cellulases are classified in EC 3.2.1.4. Cellulase endohydrolyse (1→4)-β-D-glucosidic linkages in e.g. cellulose, lichenin and cereal β-D-glucans and will also hydrolyse 1,4-linkages in β-D-glucans also containing 1,3-linkages. Cellulase also have other names such as endo-1,4-β-D-glucanase, β-1,4-glucanase, β-1,4-endoglucan hydrolase, celluase A, cellulosin AP, endoglucanase D, alkali cellulose, cellulase A 3, celludextrinase, 9.5 cellulase, avicelase, pancellase SS and 1,4-(1,3;1,4)-β-D-glucan 4-glucanohydrolase.

In one aspect of the invention, the cellulase activity of the enzyme product according to the invention is measured by "Assay 9" as described in the following under the heading "Assays". The assay can be carried out at pH 3.5 or pH 5 and 50° C. using CMC as substrate, it can be performed at different pH and temperature values for the additional characterisation and specification of enzymes. Enzyme activity is calculated from the increase in absorbance at 540 nm per unit time.

One unit of cellulase activity is defined as the amount of enzyme (normalised for total assay volume) that gives an increase in $\Delta OD_{540\ nm} \cdot min^{-1}$ under the conditions of the assay (pH 3.5 and 50° C.).

Xylanase is classified in EC 3.2.1.8, EC 3.2.1.32, EC 3.2.1.136 and EC 3.2.1.156. EC 3.2.1.8, EC 3.2.1.136 and EC 3.2.1.156 activity may be measured e.g. as described in "Assay 11".

Endo-1,4-beta xylanase is classified as EC 3.2.1.8 the enzyme causes endohydrolysis of 1,4-beta-D-xylosidic linkages in xylans.

In one aspect, the enzyme product according to the invention has endo-1,4-beta xylanase activity as measured by "Assay 11" as described in the following under the heading "Assays".

"Assay 11" can be carried out at pH 3.5 or pH 5 and 50° C. using xylan as substrate, or it can be performed at different pH and temperature values for the additional characterisation and specification of enzymes. Enzyme activity is calculated from the increase in absorbance caused by xylose at 540 nm per unit time.

One unit of xylanase activity is defined herein as the amount of enzyme (normalised for total assay volume) that gives an increase in $\Delta OD_{540\ nm} \cdot min^{-1}$ under the conditions of the assay 11 (pH 3.5 and 50° C.).

In one aspect, the enzyme product according to the invention has rhamnogalacturonase activity measured as described by e.g. Suykerbuyk et al. in "Cloning, sequence and expression of the gene coding for rhamnogalacturonase of Aspergillus aculeatus; a novel pectinolytic enzyme" Appl. Microbiol. Biotechnol. (1995) 43:861-870.

In one aspect of the invention, the enzyme product further comprises hemicellulases (or feruloyl esterase) classified in EC 3.1.1.73.

Hemicellulolytic enzymes or hemicellulases is classified in EC 3.1.1.73 and the accepted name is feruloyl esterase. They catalyse the reaction: feruloyl-polysaccharide+ $H_2O$=ferulate+polysaccharide wherein ferulate is 4-hydroxy-3-methoxycinnamate. The systematic name of hemicellulolytic enzymes is 4-hydroxy-3-methoxycinnamoyl-sugar hydrolase. It also has the following names ferulic acid esterase, hydroxycinnamoyl esterase, hemicellulase accessory enzymes; FAE-III, cinnamoyl ester hydrolase, FAEA, cinnAE, FAE-I, and FAE-II. These enzymes catalyses the hydrolysis of the 4-hydroxy-3-methoxycinnamoyl (feruloyl) group from an esterified sugar, which is usually arabinose in "natural" substrates. p-Nitrophenol acetate and methyl ferulate are poorer substrates. All microbial ferulate esterases are secreted into the culture medium. They are sometimes called hemicellulase accessory enzymes, since they help xylanases and pectinases to break down plant cell wall hemicellulose.

Laminarinase may be Endo-1,3(4)-beta-glucanase classified in E.C. 3.2.1.6 or Glucan endo-1,3-beta-D-glucosidase classified in E.C. 3.2.1.39. Endo-1,3(4)-beta-glucanase with the alternative names, Laminarinase, Endo-1,3-beta-glucanase, Endo-1,4-beta-glucanase is classified in E.C. 3.2.1.6. The substrates include laminarin, lichenin and cereal D-glucans and the enzyme catalyse Endohydrolysis of (1→3)- or (1→4)-linkages in beta-D-glucans when the glucose residue whose reducing group is involved in the linkage to be hydrolyzed is itself substituted at C-3. Glucan endo-1,3-beta-D-glucosidase with the alternative names (1→3)-beta-glucan endohydrolase, Endo-1,3-beta-glucanase and Laminarinase is classified in E.C. 3.2.1.39 and hydrolyse (1→3)-beta-D-glucosidic linkages in (1→3)-beta-D-glucans in substrates as e.g. laminarin, paramylon and pachyman.

Amylases break starch down into sugar. All amylases are glycoside hydrolases and act on α-1,4-glycosidic bonds.

Alpha-amylase (EC 3.2.1.1)(CAS #9014-71-5) (alternate names: 1,4-α-D-glucan glucanohydrolase; glycogenase): The alpha-amylases act at random locations along the starch chain, and breaks down long-chain carbohydrates, ultimately yielding maltotriose and maltose from amylose, or maltose, glucose and limit dextrin from amylopectin. Beta-amylases (EC 3.2.1.2) (alternate names: 1,4-α-D-glucan maltohydrolase; glycogenase; saccharogen amylase) Another form of amylase, working from the non-reducing end, beta-amylase catalyzes the hydrolysis of the second α-1,4 glycosidic bond, cleaving off two glucose units (maltose) at a time.

Glucoamylase (EC 3.2.1.3) (alternative names: Glucan 1,4-α-glucosidase; amyloglucosidase; Exo-1,4-α-glucosidase; glucoamylase; lysosomal α-glucosidase; 1,4-α-D-glucan glucohydrolase): In addition to cleaving the last alpa(1, 4glycosidic linkages) at the nonreducing end of amylose and amylopectin, yielding glucose, glucoamylase will cleave α(1-6) glycosidic linkages.

Holo-amylase activity is acid maltogenic activity.

"Submerged fermentation" means in the present context a type of fermentation well known by the skilled person within the field where the microorganisms are fermented submerged in a liquid medium, and preferably subjected to agitation such as continuous and vigorous agitation. The fermentation may take place in an open tank or a closed tank and may be a batch-type, fed-batch-type or a continuous-type. In batch fermentation, the organism is grown in a known amount of medium for a defined period of time and then the cell mass may be separated from the liquid before further processing while in the continuous culture, the culture medium may be withdrawn depending on the rate of product formation and the inflow of fresh medium. In a fed-batch-type fermentation at least one growth limiting compound, such as a nutrient substrate, is fed to the fermentation broth during fermentation.

A product with similar activities may be obtainable by surface fermentation of *Aspergillus*, however, handling of surface fermentation is in practice difficult and the enzyme product is to be purified or extracted from the surface. Furthermore, in order to avoid infection from other microorganisms it is simpler to sterilize a liquid medium for submerged fermentation by methods well-known to the skilled person such as by heat treatment or by acidic pH treatment than sterilizing a solid medium for surface fermentation. It is also more convenient to control and adjust the pH value during submerged fermentation by addition of pH adjusting agents in order to keep the medium at an optimal pH value and/or constant pH value. For these and other reasons submerged fermentation is therefore a far more preferred method in industrial scale than surface fermentation.

In one aspect, the strain is from the *Aspergillus niger* group. In a further aspect, the strain is *Aspergillus tubingensis*. *A. tubingensis* is a member of the *A. niger* group.

In yet a further aspect, *Aspergillus tubingensis* having the deposit accession number CBS123488 or a derivative or progeny thereof, is provided.

In yet a further aspect, the strain used for the fermentation has characteristics substantially identical to that of the strain *Aspergillus tubingensis* having the deposit accession number CBS123488.

In a further aspect, the strain is an *Aspergillus tubingensis* having the deposit accession number CBS123488.

In the context of the present invention, the phrase "characteristics substantially identical" means that the strain has one or more (preferably all) of the characteristics of the *Aspergillus tubingensis* having the deposit accession number CBS123488 deposited at the Centraalbureau voor Schimmelcultures, Uppsalalaan 8, NL-3584 CT Utrecht, The Netherlands/P.O. Box 85167, NL-3508 AD Utrecht, The Netherlands and given the following accession numbers: CBS 123488 *Aspergillus tubingensis* 4 M 146 and the date of deposit Sep. 30, 2008.

It is to be understood that a fungal strain used in accordance with the invention may be a culture of the above mentioned deposited strain, but may also be a culture of a strain which has properties substantially identical to the above mentioned isolated and deposited strain. In a preferred embodiment the strain is the deposited strain or a progeny thereof.

In one aspect of the invention, the single fungal culture of the strain *Aspergillus* is selected from the group of *Aspergillus niger* 402 (such as CBS 120.49), *Aspergillus niger* hennebergii (such as CBS 117.80), *Aspergillus carbonarius* (such as CBS 112.80, CBS 420.64), *Aspergillus niger* nanus (such as CBS 136.52, CBS 117.48), *Aspergillus foetidus* (such as CBS 121.78, CBS 618.78), *Aspergillus tubigensis* (such as CBS 11529), *Aspergillus niger* intermedius (such as CBS 559.65) and *Aspergillus japonicus* (such as CBS 114.51, CBS 621.78), *Aspergillus aculeatus* (such as CBS 101.43, CBS 115.80, CBS 172.66, CBS 119.49), *Aspergillus caesiellus*, *Aspergillus candidus*, *Aspergillus carneus*, *Aspergillus clavatus*, *Aspergillus deflectus*, *Aspergillus flavus*, *Aspergillus fumigatus*, *Aspergillus glaucus*, *Aspergillus nidulans*, *Aspergillus niger*, *Aspergillus ochraceus*, *Aspergillus oryzae*, *Aspergillus parasiticus*, *Aspergillus penicilloides*, *Aspergillus restrictus*, *Aspergillus sojae*, *Aspergillus sydowi*, *Aspergillus tamari*, *Aspergillus terreusm*, *Aspergillus ustus*, or *Aspergillus versicolor*.

In one aspect of the invention, the *Aspergillus* strain has not been genetically modified.

In one aspect of the invention, an enzyme product preparation comprising the enzyme product according to the invention, an enzyme carrier and optionally a stabilizer and/or a preservative, is provided.

In yet a further aspect of the invention, the enzyme carrier is selected from the group consisting of glycerol or water.

In a further aspect, the preparation comprises a stabilizer. In one aspect, the stabilizer is selected from the group consisting of inorganic salts, polyols, sugars and combinations thereof. In one aspect, the stabilizer is an inorganic salt such as potassium chloride. In another aspect, the polyol is glycerol or sorbitol. In yet another aspect, the sugar is a small-molecule carbohydrate, in particular any of several sweet-tasting ones such as glucose, fructose and saccharose.

In yet at further aspect, the preparation comprises a preservative. In one aspect, the preservative is methyl paraben, propyl paraben, benzoate, sorbate or other food approved preservatives or a mixture thereof.

The enzyme product according to the invention has several advantages e.g. in the production of fruit juice. In one aspect, increased yield due to easier liquid/solid separation and higher juice yield is provided. In one aspect, higher capacity, regardless of the equipment used (horizontal presses, belt presses or decanters) due to the reduced viscosity of the mash and secondary mash, is provided. In one aspect, less pomace as higher juice yields have a direct influence on the quantity of leftover pomace, is provided. In one aspect, easier cleaning of the press, is provided. In one aspect, less pectin in the juice, is provided. In one aspect, fast, effective viscosity reduction of the mash, is provided. In one aspect, good solid/liquid separation in all systems and high juice yield, is provided. In one aspect, highly efficient color extraction and stable color in juices and concentrates, is provided.

In one aspect of the invention, the pectin lyase activity in the enzyme product preparation according to the invention is in the range of 50-10.000 U/g, preferably in the range of 75-7000 U/g and more preferably in the range of 100-5000 U/g e.g. as measured in "Assay 3" as described in the following.

In a further aspect, the pectinesterase activity in the enzyme product preparation according to the invention is in the range of 10-10000 U/g preferably in the range of 100-7000 U/g and more preferably in the range of 500-3000 U/g e.g. as measured in "Assay 7" as described in the following.

In yet a further aspect, the arabinanase activity in the enzyme product preparation according to the invention is in the range of 10-8000 U/g, preferably in the range of 50-4000 U/g and more preferably in the range of 100-2500 U/g e.g. as measured in "Assay 8" as described in the following.

In yet a further aspect, the cellulase activity in the enzyme product preparation according to the invention is in the range of 10-5000 U/g, preferably in the range of 50-4000 U/g and more preferably in the range of 100-2000 U/g e.g. as measured in "Assay 9" as described in the following.

In yet a further aspect, the endo-1,4-xylanase activity in the enzyme product preparation according to the invention is in the range of 10-10.000 U/g, preferably in the range of 50-10.000 U/g and more preferably in the range of 100-7000 U/g e.g. as measured under the conditions of "Assay 11" (pH 3.5 and 50° C.).

In one aspect, the enzyme product is used in production of fruit juice concentrates and wine.

The enzyme product according to the invention may be used as a supplement to the enzymes naturally present in fruit, and may accelerate and enhance the processing of apples, pears, grapes and citrus fruits.

In one aspect of the invention, the enzyme product may be used such as e.g. in citrus fruit processing, wherein the application of enzymes reduces juice viscosity, eliminating the risk of jellification during fruit juice concentration and storage and securing high cloud stability. Applied during the pulp extraction process, the enzyme product according to the invention facilitates the release of juice and solids, increasing yield and improving cost efficiency. A stable cloud—or, in the case of lemon juice, successful clarification—is an important measure of the final product's superior quality.

Essential citrus oils can also be recovered while using the enzyme product according to the invention in citrus fruit processing. Apart from providing access to a valuable commodity, citrus oil recovery is important from a sustainability point of view, ensuring a low content of the bactericidal oils in wastewater for improved wastewater biodegradability and reducing overall water consumption. In one aspect of the invention, the enzyme product is used for clarification of lemon juice. In one aspect of the invention, the enzyme product is used in citrus fruit processing for pulp/core wash, viscosity reduction of citrus juice and/or peel extraction.

The production of high clarity apple and pear juice is dependent on the complete breakdown of starch and pectin content. This may be achieved by the addition of the enzyme product to the juice before clarification and filtration. Added to the fruit mash before pressing and juice separation, the enzyme product may lead to a reduction in mash viscosity, resulting in increased juice yield and optimised processing capacity. Less waste pomace and easier cleaning of fruit presses may be other value-adding advantages. In one aspect of the invention, the enzyme product is used for maceration of apple and pear mash. In one aspect of the invention, the enzyme product is used for extraction of apple pomace after initial pressing. In one aspect of the invention, the enzyme product is used for starch degradation in apple and pear juice. In one aspect of the invention, the enzyme product is used for pectin degradation in fruit juice, especially apple juice. In one aspect of the invention, the enzyme product is used for pectin and araban degradation in fruit juice, especially pear juice.

Winemakers need to produce high quality wines year after year, regardless of annual variations in the weather. The enzyme product according to the invention may aid in transferring valuable components, such as aromas, colour and tannins, from the grape to the wine, and may help to preserve wine quality, sometimes over many years in storage. The enzyme product may also reduce fermentation time and promote clarification, filtration and stabilisation.

The invention is also directed at any products derived from the abovementioned processes. Such products comprise beverages derived from plant material, e.g. fruit juice, coffee, tea, beer, wine, cider and nutritional preparations and ingredients for foodstuffs, e.g. for baby food and new maceration and/or liquefaction products.

In one aspect, a use of an enzyme product or an enzyme product preparation for the degradation of plant material such as wherein the plant material is a plant cell, such as wherein the plant material is a plant cell wall or a part thereof, such as for releasing a compound e.g. where the compound is a biologically active compound or a precursor thereof, such as wherein the compound is a pharmaceutical active compound, is provided. In one aspect, the plant material is genetically modified. In a further aspect, use of an enzyme product for the degradation of waste, is provided. In yet a further aspect, use of an enzyme product during fruit juice and/or wine manufacture in the steps of extraction and/or liquefaction of fruit and/or fruit juice clarification, is provided.

Further applications of the enzyme product and/or enzyme product preparation comprise applications, where it is desired to extract a colour/pigment from a plant material, such as a fruit, such as e.g. the red colour of a berry (e.g. blackcurrant, redcurrant, gooseberry, cranberry, blueberry, blackberry, raspberry, boysenberry, mulberry, strawberry and the like), or other fruits (e.g. guava, lucuma, pomegranate, kiwifruit, grape, pumpkin, gourd, cucumber, melon orange, lemon, lime, grapefruit, banana, hedge apple, pineapple, fig, apple, quince, pear, rose hip, peach, cherry, date, mango, nectarine, plum, apricot, etc. A further application of the enzyme product and/or enzyme product preparation comprise colour extraction from grapes for fruit juice or wine production, such as red wine and rosé production. In colour/pigment extractions from a plant material it is usually desired to extract as much colour/pigment as possible.

The concentration of the enzyme product according to the invention in the final preparation depends on the use envisaged.

In the preparation for use the enzyme product is typically used in a dosage of 4-300 ppm. For many usages the enzyme product is adjusted by dilution or concentration to an activity of about 300-600 U/g as measured by "Assay 3" as pectin lyase activity. The remaining enzyme activities are thereafter determined after the adjustment of the enzyme product to a pectin lyase activity of about 300-600 U/g as measured by "Assay 3". However, the activity per gram of any enzyme is of course dependant on the dilution or concentration of either the enzyme product obtained from the fermentation or the final preparation.

If the enzyme activity of the enzyme product is in the range of 100-800 U/g (pectin lyase units) then the activity in the final application can be calculated as:

Minimum: 4 ppm (g/tons) of a 100 U/g product results in a concentration of enzyme in the final application: 0.4 U/kg Maximum: 300 ppm of a 800 U/g product results in a concentration of enzyme in the final application: 240 U/kg The relevant dosage in a particular application depends on temperature, pH and holding time.

In one aspect of the invention, the concentration in the application product pr. kg product is 0.001 U/kg-10.000 U/kg, wherein the application product for example is a fruit juice such as apple, pear, grape or citrus fruit.

In one aspect of the invention, the concentration in the application product pr. kg product is 0.005 U/kg-5.000 U/kg, wherein the application product for example is a fruit juice such as apple, pear, grape or citrus fruit. In one aspect of the invention, the concentration in the application product pr. kg product is 0.05 U/kg-2000 U/kg.

In one aspect of the invention, the concentration in the application product pr. kg product is 0.1 U/kg-500 U/kg, wherein the application product for example is a fruit juice such as apple, pear, grape or citrus fruit. In one aspect of the invention, a fruit juice such as apple, pear, grape or citrus fruit juice comprising an enzyme product preparation according to the invention, is provided.

In one aspect of the invention, a process for the production of an enzyme product according to the invention is provided.

In one aspect, a process for the production of an enzyme product, which process comprises the steps of submerged fermentation of *Aspergillus tubingensis* in a medium to obtain a fermentation broth, and optionally recovery of the enzyme product in the form of a cell free broth from said fermentation broth, is provided. In a further aspect, a process comprising the steps of submerged fermentation of one single culture of *Aspergillus tubingensis* in a medium to obtain a fermentation broth, and optionally recovery of the enzyme product in the form of a cell free broth from said fermentation broth, is provided.

In one aspect, a process for the production of an enzyme product, where said process comprises the steps of submerged fermentation of *Aspergillus* in a medium which medium comprises sugar beet pulp to obtain a fermentation broth, and optionally recovery of the enzyme product in the form of a cell free broth from said fermentation broth, is provided. In a further aspect, a process comprising the steps of submerged fermentation of one single culture of *Aspergillus* in a medium comprising sugar beet pulp to obtain a fermentation broth, and optionally recovery of the enzyme product in the form of a cell free broth from said fermentation broth, is provided.

In a further aspect, the fermentation comprises the steps of:
a. growing said *Aspergillus* strain such as *Aspergillus* culture in a inoculum medium to obtain an inoculum, and
b. adding said inoculum to a fermentation medium comprising vegetable material comprising pectin and arabinan.

In one aspect, the inoculum medium comprises sugar beet pulp and/or cereal bran such as wheat bran. In one aspect, the inoculum medium comprises sugar beet pulp and cereal bran such as wheat bran.

In one aspect of the invention, a process for the production of an enzyme product by submerged fermentation comprising the steps of:
a. growing one single culture of *Aspergillus* in an aerated seed substrate medium optionally comprising cereal bran and/or sugar beet pulp, the substrate medium having a pH in the range of 2-8 to obtain an inoculum,
b. adding said inoculum to a fermentation medium comprising cereal bran and sugar beet pulp and incubating said inoculated fermentation medium under air in order to obtain a fermentation broth, and
c. recovering the enzyme product from said fermentation broth, is provided.

In a further aspect of the invention, a process for the production of an enzyme product comprising the steps of:
a. growing one single culture of *Aspergillus* in an aerated seed medium optionally comprising cereal bran and/or sugar beet pulp, the medium having a pH in the range of 2-8 for a period of 10 to 60 hours to obtain an inoculum,
b. adding said inoculum at a concentration in the range of 10-20% (V/V) to a fermentation medium comprising cereal bran and sugar beet pulp and incubating said fermentation medium for a period of 20 to 140 hours under air in order to obtain a fermentation broth, and
c. recovering the enzyme product from said fermentation broth, is provided.

In the first step (a), the production strain is cultivated or grown in a medium containing previously-sterilized raw materials and water. The medium for the fermentation process can be made of many different raw materials. In one aspect of the invention, the medium used for growing said fungal culture to obtain an inoculum comprises sugar beet pulp and optionally cereal bran. In one aspect, the medium is sterilized by acidic pH treatment such as by treatment at a pH in the range of 2-7, at a pH in the range of 2.25-6, at a pH in the range of 2.5-5, at a pH in the range of 3-4 or at a pH at approximately 3.5. In a further aspect, the medium is sterilized by acidic pH treatment such as by a pH treatment at a pH-value of at least 2, of at least 2.5 or of at least 3.

In a further aspect of the invention, the fermentation medium used for said submerged fermentation in step (b) comprises cereal bran. In another aspect of the invention, the medium used for said submerged fermentation comprises both cereal bran and sugar beet pulp.

The present invention may be useful for any submerged fermentation in industrial scale, e.g., for any fermentation having culture media of at least 5 L. In a further aspect, the fermentation may be performed in a culture media of 50 L, 500 L 5000 L, 50000 L or 150 m3.

In one aspect, the invention relates to an enzyme product obtainable by the process according to the invention.

In one aspect of the invention, a foam inhibitor is added during the fermentation. As examples of antifoam agents mention may be made of a polypropylene glycol based blend e.g. Erol DF 6000K (CAS 009082-00-2) or e.g. SIN260.

In one aspect of the invention, the pH in step (a) and/or step (b) is in the range of 2-8. In one aspect of the invention, the pH in step (a) and/or step (b) is in the range of 2.5-6. In one aspect of the invention, the pH in step (a) and/or step (b) is in the range of 3-4.5, such as in the range of 3-4 such as in the range of 3.2-3.7 or such as in the range of 3.3-3.7. In one aspect of the invention, the pH in step (a) and/or step (b) is in the range of 3.3-3.7.

In one aspect of the invention, the temperature in step (a) and/or step (b) is in the range of 25-40° C. In one aspect of the invention, the temperature in step (a) and/or step (b) is in the range of 28-34° C.

In one aspect of the invention, the submerged fermentation is being conducted as aerobic fermentation.

In one aspect of the invention, the growing of the culture of *Aspergillus* in step (a) in an aerated seed medium comprising cereal bran and sugar beet pulp and the medium having a pH in the range of 2-8 is for a period of 10 to 60 hours. In another aspect, the growing is for a period from 15 to 50 hours, such as from 20 to 40 hours.

In one aspect of the invention, the pH in step (b) is adjusted to pH 2-8, such as 2.5-6 e.g. pH 3-4. The culture is incubated in step (b) at a temperature in the range of 20-45° C. In one aspect of the invention, the culture is incubated in step (b) at a temperature in the range of 25-35° C. In another aspect of the invention, the culture is incubated in step (b) at a temperature in the range of 28-34° C. In one aspect, the culture is incubated in step (b) for a period of 40 to 140 hours during aeration. In another aspect, the culture is incubated in step (b) for a period from 60 to 120, such as from 70 to 110 hours during aeration.

The temperature profile may be kept constant or varied during fermentation within the stated intervals.

In a one aspect of the invention, both the medium for growing the culture in step (a) and the fermentation medium in step (b) comprises cereal bran and sugar beet pulp.

In a further aspect, the medium comprises potassium nitrate. In a further aspect, the medium comprises ammonium sulphate. In a further aspect, the medium comprises both ammonium sulphate and potassium nitrate. In a further aspect the medium comprises cereal bran, sugar beet pulp, ammonium sulfate, and potassium nitrate in water.

In one aspect of the invention, the cereal bran is in the form of wheat bran pellets. Wheat bran pellets may be made from wheat bran, a by-product of flour and grits production, which predominantly consists of husks and variable proportions of the endosperm, by adding a suitable binder (e.g. 1-3% (w/w) of molasses, fat or colloidal clays) and then pressing the composition under high pressure in pelletizing machines or extruders to form cylindrically shaped pellets. Pellets generally have the same characteristics as the original plant residues, in particular in terms of the product's oil and water content. A distinction is drawn between expeller pellets and extraction meal pellets depending on their origin.

Bran is the hard outer layer of grain and comprises combined aleurone and pericarp. Along with germ, it is an integral part of whole grains, and can be produced as a by-product of milling in the production of refined grains. Bran is particularly rich in dietary fiber and may contain significant quantities of starch, protein, vitamins, and dietary minerals. The relatively high oil content of bran makes it subject to rancidification, one of the reasons why it is often separated from the grain before storage or further processing. The bran itself can be heat-treated to increase its longevity.

When bran is removed from grains, they lose a portion of their nutritional value. Bran is present in and may be milled from any cereal grain, including rice, corn, wheat, maize, oats, barley and millet.

Rice bran is a by-product of the rice milling process (the conversion of brown rice to white rice). Rice makes up the genus *Oryza* of the family Poaceae (or Gramineae), common rice is classified as *Oryza sativa*.

In the present context, the term "wheat bran" relates to a product comprising the hard outer layer of wheat grain and comprises combined aleurone and pericarp. In one aspect, the wheat bran has an arabinan content of 2-20% w/w. In one aspect, the wheat bran has an arabinan content of 5-15% w/w. In one aspect, the wheat bran comprises at least 2% w/w arabinan, such as at least 3% w/w arabinan, such as at least 4% w/w arabinan, or such as at least 5% w/w arabinan.

In a further aspect, the wheat bran is present in the fermentation medium in the range of 3-7% w/w. In a further aspect, the wheat bran is present in the fermentation medium in the range of 3.5-6% w/w. In a further aspect, the wheat bran is present in the fermentation medium in the range of 4-5% w/w.

In one aspect, the flour concentration in the wheat bran is low.

Likewise, it is believed that sugar beet pulp pellets should preferably not be molasse-treated. Commercially available products (e.g. "pulpetter") are believed to be suitable. It is also believed that the amount of water that can be absorbed by the pellets can be an indicator of quality, such as the ability of absorbing ~4× their weight in water (good quality) compared to e.g. ~2× (inferior quality).

Due to possible variations in raw-material quality (batch to batch, season to season, supplier to supplier etc.), it is suggested to test these for their suitability for the preparation of an enzyme product on a smaller scale.

In one aspect of the invention, sugar beet pulp is used both in the substrate medium under a) and in the fermentation medium under b). Sugar beet (Beta vulgaris L.), a member of the Chenopodiaceae family, is a plant whose root contains a high concentration of sucrose. It is grown commercially for sugar. The sugar beet is directly related to the beetroot, chard and fodder beet, all descended by cultivation from the sea beet.

In one aspect of the invention, the sugar beet pulp is in the form of sugar beet pellets or dried beet pulp or granulated beet pulp.

Sugar beet pulp is the vegetable material, which remains after sugar is extracted from sliced sugar beets. After being harvested, the sugar beets are hauled to a factory, where they are tipped onto the reception area, typically a "flat pad" of concrete, where it is moved into large heaps. The beet is moved from the heaps into a central channel or gulley, where it is washed towards the processing plant. After reception at the processing plant, the beet roots are washed, mechanically sliced into thin strips called cossettes, and passed to a machine called a diffuser to extract the sugar content into a water solution. Diffusers are long vessels of many meters in which the beet slices go in one direction while hot water goes in the opposite direction. The movement may either be by a rotating screw or the whole unit rotates, and the water and cossettes move through internal chambers. There are different designs of diffuser, e.g. horizontal rotating, inclined screw, or vertical screw "Tower". A less common design uses a moving belt of cossettes, with water pumped onto the top of the belt and poured through. Often, the flow rates of cossettes and water are in the ratio one to two. Typically cossettes take about 90 minutes to pass through the diffuser, the water only 45 minutes. These are all countercurrent exchange methods that extract more sugar from the cossettes using less water than if they merely sat in a hot water tank. The liquid exiting the diffuser is called raw juice. The colour of raw juice varies from black to a dark red depending on the amount of oxidation, which is itself dependent on diffuser design. The used cossettes, or pulp, exits the diffuser at about 95% moisture but low sucrose content. Using screw presses, the wet pulp is then pressed down to 75% moisture. This recovers additional sucrose in the liquid pressed out of the pulp, and reduces the energy needed to dry the pulp. The pressed pulp can be dried and sold, e.g. as animal feed. This vegetable material may then be made into pellets to improve its nutritional value and handling characteristics. It is high in fiber and unique in that its fiber is extremely digestible.

In a further aspect of the invention, sugar beet pulp is in the form of beet pellets obtained from Danisco Sugar A/S. In another aspect of the invention, the sugar beet pulp is in the form of FIBREX® (sugar beet fiber) beet pellets obtained from Nordic Sugar.

The beet pulp may be molassed or un-molassed, preferably un-molassed such as FIBREX® (sugar beet fiber). Molasses or treacle is a thick syrup by-product from the processing of the sugarcane or sugar beet into sugar. The quality of molasses depends on the maturity of the sugar cane or beet, the amount of sugar extracted, and the method of extraction.

In one aspect of the invention, the substrate used for the submerged fermentation comprises sugar beet pulp in the range of 1-30% w/w. In another aspect, the substrate used for the submerged fermentation comprises sugar beet pulp in the range of 1-20%, 2-20%, 1-15%, 1-10%, 3-15%. In a further aspect, the sugar beet pulp is present in the fermentation medium in the range of 2-8% w/w. In a further aspect, the sugar beet pulp is present in the fermentation medium in the range of 3-7% w/w. In a further aspect, the sugar beet pulp is present in the fermentation medium in the range of 4-7% w/w. In a further aspect, the sugar beet pulp is present in the fermentation medium in the range of 3.5-6% w/w. In a further aspect, the sugar beet pulp is present in the fermentation medium in the range of 4-6% w/w. In a further aspect, the sugar beet pulp is present in the fermentation medium in the range of 4-5% w/w. In one aspect, the sugar beet pulp is present in the fermentation medium in an amount of at least 2% w/w, such as at least 3% w/w or such as at least 4% w/w.

In one aspect of the invention, the sugar content in the sugar beet pulp used is approximately in the range of 0.5-20% (w/w). In a further aspect, the sugar beet pulp has a sugar content of 1-10% w/w. In a further aspect, the sugar beet pulp has a sugar content of 2-8% w/w on dry basis. In one aspect, the sugar content in the sugar beet pulp used is in an amount of at least 0.5% w/w, such as of at least 2% w/w, such as of at least 4% w/w, such as of at least 6% w/w, or such as at of least 8% w/w.

In a further aspect of the invention, the pectin content in the sugar beet pulp used is approximately in the range of 8-35% w/w on dry basis, approximately in the range of 12-28% (w/w), approximately in the range of 15-22% w/w on dry basis. In one aspect, the pectin content in the sugar beet pulp used is in an amount of at least 9% w/w, such as of at least 11% w/w, such as of at least 13% w/w or such as of at least 15% w/w.

In one aspect of the invention, the sugar beet pulp has an arabinan content of 1.5-40% w/w on dry basis. In one aspect of the invention, the sugar beet pulp has an arabinan content of 5-40% w/w on dry basis. In one aspect of the invention, the sugar beet pulp has an arabinan content of 10-30% or 5-30% w/w on dry basis. These ranges may vary depending on the specific type of sugar beet pulp used. In one aspect, the sugar beet pulp comprises at least 1.5% w/w arabinan, such as at least 2% w/w arabinan, such as at least 3% w/w arabinan, such as at least 4% w/w arabinan, such as at least 5% w/w arabinan, such as at least 6% w/w arabinan, such as at least 7% w/w arabinan, such as at least 8% w/w arabinan, such as at least 9% w/w arabinan or such as at least 10% w/w arabinan.

In one aspect, the vegetable material which comprises pectin and arabinan to be used in the fermentation medium is a mixture of cereal bran (e.g. wheat bran) and sugar beet pulp in a ratio of approximately 20:80 to 80:20, 30:70 to 70:30, 40:60 to 60:40 or 45:55 to 55:45 (w:w). In a further aspect, the mixture of cereal bran (e.g. wheat bran) and sugar beet pulp is in a ratio of approximately 50:50, approximately 45:55: approximately 55:45; approximately 40-60; approximately 60:40; approximately 30:70; approximately 70:30; approximately 20:80; approximately 80:20 (w:w). In one aspect, the mixture contains more sugar beet pulp than cereal bran (e.g. wheat bran) such as in a ratio of approximately 51:49 to 60:40 or approximately 51:49 to 55:40 (w:w). In one aspect, the mixture contains more sugar beet pulp than cereal bran (e.g. wheat bran) such as in a ratio of approximately 51:49, approximately 52:48 to, approximately 53-47, or approximately 54:46 (w:w).

In a further aspect, the sugar beet pulp and the wheat bran each is present in the fermentation medium in the range of 3-7% w/w. In a further aspect, the sugar beet pulp and the wheat bran each is present in the fermentation medium in the range of 3.5-6% w/w. In a further aspect, the sugar beet pulp and the wheat bran each is present in the fermentation medium in the range of 4-6% w/w. In a further aspect, the sugar beet pulp and the wheat bran each is present in the fermentation medium in the range of 4-5% w/w, such as each present in an amount of approximately 4% w/w, approximately 4.2% w/w, approximately 4.3% w/w, approximately 4.4% w/w, approximately 4.5% w/w, approximately 4.6% w/w, approximately 4.7% w/w, approximately 4.8% w/w, approximately 4.9% w/w or approximately 5.0% w/w.

In the present context, the term "broth" and "medium" means a liquid medium containing a variety of nutrients that is used to grow (ferment) a culture(s) of a microorganism(s).

In one aspect of the invention, the fermentation medium used comprises cereal bran such as wheat bran and sugar beet pulp. In some embodiments, it has been found that the use of both cereal bran such as wheat bran and sugar beet pulp in the fermentation medium result in an enzyme product having a high overall enzymatic activity and many different enzymatic activities both in terms of different enzymes and many different side-activities. In some embodiments, it has also been found that the use of both cereal bran such as wheat bran and sugar beet pulp in the fermentation medium result in an enzyme product having enzyme activities such as arabinofuranosidase and arabinanase.

In a further aspect of the invention, the fermentation medium used in the step (b) has the following composition: cereal bran, sugar beet pulp, ammonium sulfate, and potassium nitrate. The pH of the medium may be adjusted by the addition of sulfuric acid.

Different methods may be used for deciding when the fermentation is completed. The fermentation may be followed by measuring the viscosity of the medium. This is common practice for a skilled person within the field and the measurement may be performed by using a viscosity meter A&D Company of the type Vibro Viscometer SV-10. The viscosity at the beginning of the fermentation is typically >150 mPa·s such as >200 mPa·s and the fermentation may be stopped when the viscosity is <150 mPa·s such as below 100 mPa·s, below 75 mPa·s or below 50 mPa·s.

In one aspect of the present invention, the fermentation medium used has the following composition:

| Ingrediens | Proportion (w/w %) |
|---|---|
| Wheat Bran | 3-8 |
| Sugar beet pulp pellets | 2-10 |
| Ammonium sulfate | 0-1.0 such as 0.3-1.0 |
| Potassium nitrate | 0.1-0.6 |

In one aspect of the invention, the pH is adjusted using sulfuric acid and/or sodium hydroxide.

After the fermentation the enzyme product may be recovered by the use of conventional processes by which the biomass is separated from the supernatant, where the biomass includes cells, and "left-overs" of e.g. wheat bran and sugar beet pulp pellets.

The purpose of the recovery process is in one aspect to separate the biomass, purify, concentrate, and stabilize the desired enzyme mixture. The pectolytic enzymes are extracellular and the enzymes formed during fermentation are thus excreted into the liquid (the supernatant).

The first objective in processing the harvested fermentation broth is to separate the cells from the broth. This separation is usually achieved by filtration such as by the use of a rotary vacuum filter followed by concentration which is usually done by ultrafiltration or evaporation.

In the case of products with high purity demands, the downstream process may often require a special step to remove unwanted impurities. This may be done by selective precipitation or adsorption of the impurities, or crystallisation by which extremely pure enzyme products can be obtained.

After the biomass has been separated, the supernatant of enzyme product may be concentrated depending of the required strength needed. The supernatant may be concentrated such as for example 5 times, 10 times, 15 times or 20 times. Ultra filtration may be used to achieve the required strength. By ultra filtration the supernatant of the enzyme product is separated into a concentrated supernatant and a permeate, the permeate is mainly pure water. The concentrated supernatant of enzyme product may then be filter sterilized to obtain a concentrated and sterilized enzyme product.

In one aspect of the invention, especially when the product is intended for usage in the food industry, the concentrated enzyme solution from the steps described above may be standardized and stabilized with food grade formulation and preservation agents. During this part of the process, the enzyme activity of the preparation may be standardized to the desired commercial level for the intended commercial enzyme preparation and adjusted for pH. In some embodiments a pH adjustment of the finished enzyme product to e.g. pH 3.5 is believed to increase stability/storageability of the finished product.

A polish filtration step may be applied, in which perlite and/or diatomaceuous earth may be used. The polish filtration may be performed by either of the following methods: pancake filter, filter cartridge or by filterpress.

The enzyme product may be dried e.g. by spray drying or freeze drying. For drying a carrier may be needed such as malto dextrins or KCl.

The enzyme product can be formulated as liquid, powder or granulated using conventional means and methods known in the art.

One embodiment of the process using the strain *Aspergillus tubingenesis* for the production of the enzyme product according to the invention in the form of a filtrate/supernatant (which for use may be concentrated) may be illustrated as shown below:

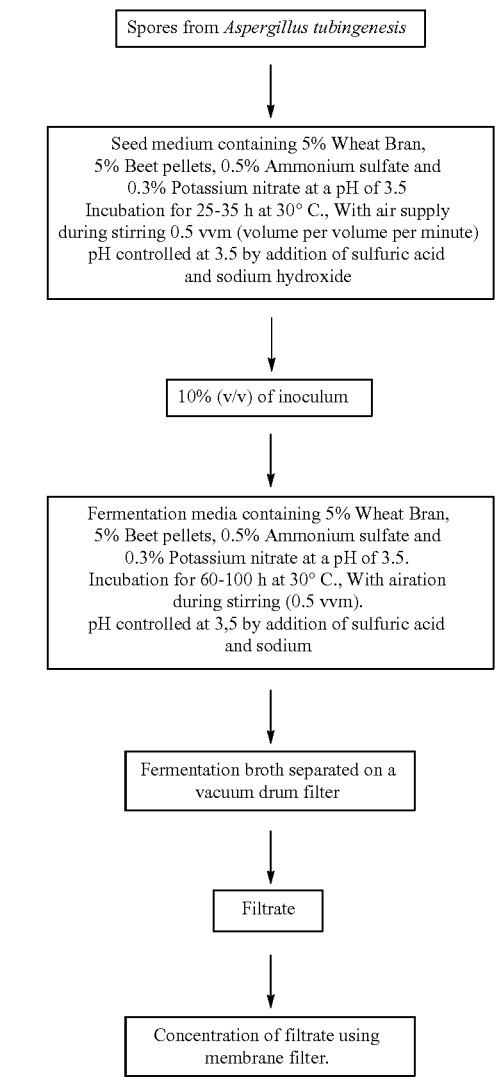

In the above "beet pellets" means "sugar beet pulp pellets".

Further embodiments according to the invention:

1. An enzyme complex comprising at least the following enzyme activities:
   i. endo-polygalacturonase activity
   ii. exo-polygalacturonase activity
   iii. pectinesterase activity
   iv. pectin lyase activity
   v. cellulase activity
   vi. xylanase activity and
   vii. arabinanase activity
and where said enzyme complex is an expression product obtained by submerged fermentation of an *Aspergillus* strain.

2. The enzyme complex according to embodiment 1, wherein said enzyme complex is an expression product obtained by submerged fermentation of one single culture of the *Aspergillus* strain.

3. The enzyme complex according to any one of the embodiments 1-2 further comprising rhamnogalacturonase activity.

4. The enzyme complex according to any one of the embodiments 1-3 further comprising hemicellulases activity.

5. The enzyme complex according to any one of the embodiments 1-4 further comprising glucoamylase activity.

6. The enzyme complex according to any one of the embodiments 1-5 further comprising holoamylase activity.

7. The enzyme complex according to embodiment 1, wherein said strain is from the *Aspergillus niger* group.

8. The enzyme complex according to embodiment 1, wherein said strain is *Aspergillus tubingensis*.

9. The enzyme complex according to embodiment 7, wherein said strain is *Aspergillus tubingensis* having the deposit accession number CBS123488.

10. The enzyme complex according to any one of the embodiments 1-9, where the medium used for said submerged fermentation comprises sugar beet pulp.

11. The enzyme complex according to any one of the embodiments 1-9, where the medium used for said submerged fermentation comprises cereal bran, such as wheat bran.

12. The enzyme complex according to any one of the embodiments 1-11, where the medium used for the submerged fermentation comprises sugar beet pulp in the range of 1-30% (w/v).

13. The enzyme complex according to any one of the embodiments 1-12 having a higher endo-polygalacturonase activity than exo-polygalacturonase activity.

14. The enzyme complex according to any one of the embodiments 1-13, wherein the *Aspergillus* strain has not been genetically modified.

15. An enzyme complex preparation comprising the enzyme complex according to any one of the embodiments 1-14, an enzyme carrier and optionally a stabilizer and/or a preservative.

16. A process for the production of an enzyme complex, the process comprising the steps of submerged fermentation of *Aspergillus tubingensis* in a medium to obtain a fermentation broth, and recovery of the enzyme complex in the form of a cell free broth from said fermentation broth.

17. A process for the production of an enzyme complex, the process comprising the steps of submerged fermentation of *Aspergillus* in a medium which medium comprises sugar beet pulp to obtain a fermentation broth, and recovery of the enzyme complex in the form of a cell free broth from said fermentation broth.

18. The process according to any one of the embodiments 16-17, wherein the fermentation comprises the steps of:
   a. growing said culture in a medium to obtain an inoculum, and
   b. adding said inoculum to a fermentation medium comprising sugar beet pulp and/or cereal bran.

19. The process according to any one of the embodiments 16-18, wherein the medium to obtain said inoculum comprises sugar beet pulp.

20. The process according to any one of the embodiments 16-19, wherein the pH during the fermentation is in the range of 2-8.

21. The process according to any one of the embodiments 16-19, wherein the pH during step the fermentation is in the range of 2.5-6.

22. The process according to any one of the embodiments 16-19, wherein the pH during the fermentation is in the range of 3-4.

23. The process according to any one of the embodiments 16-19, wherein the pH during the fermentation is in the range of 3.3-3.7.

24. The process according to any one of the embodiments 16-23, wherein the temperature during the fermentation is in the range of 25-40° C.

25. The process according to any one of the embodiments 16-23, wherein the temperature during the fermentation is in the range of 28-34° C.

26. The process according to any one of the embodiments 16-25, wherein the fermentation is conducted as aerobic fermentation.

27. The process according to any one of the embodiments 16-26, wherein the medium used for said fermentation comprises both sugar beet pulp and cereal bran.

28. The process according to any one of the embodiments 16-27, wherein the medium further comprises ammonium sulphate and/or potassium nitrate.

29. The process according to any one of the embodiments 16-28, where the medium used for the submerged fermentation comprises sugar beet pulp in the range of 1-30% by weight.

30. The process according to any one of the embodiments 16-29, where the enzyme complex obtained is as defined in any one of the embodiments 1-15.

31. An enzyme complex obtainable by a process according to any one of embodiments to any one of the embodiments 16-29.

32. *Aspergillus tubingensis* having the deposit accession number CBS123488 or a derivative or progeny thereof.

33. An isolated *Aspergillus tubingensis* having the deposit accession number CBS123488 or a derivative or progeny thereof.

34. A fungal culture having characteristics substantially identical to that of the strain *Aspergillus tubingensis* having the deposit accession number CBS123488.

35. The culture of embodiment 34, wherein the culture has properties identical to the deposited strain.

36. The culture of embodiment 34, wherein the culture is the deposited strain or progeny thereof.

All publications mentioned herein are incorporated by reference. The terms "a" and "an" and "the" and similar referents as used in the context of describing the invention are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).). "About" or "~" can e.g. be common analytical variations known in the art and/or variations of e.g. +/−1, 5, or 10%.

Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry, microbiology and molecular biology or related fields are intended to be within the scope of the following claims.

EXAMPLES

General Method a) A culture of *Aspergillus tubingensis* is grown on a sterilized medium containing Wheat Bran (5% W/W), Sugar beet pulp pellets (5% W/W), Ammonium sulfate (0.5% W/W), Potassium nitrate (0.3% W/W) in water, with pH adjusted to pH 3-4. The culture is incubated at a temperature in the range of 25-35° C. for a period of 24 to 48 hours and aerated during stirring with 0.3 to 1 vvm sterile air (volume per volume per minute) in order to obtain an inoculum.

b) The inoculum, obtained in step (a), is added to the fermentation media at a concentration in the range of 10-20% (V/V) followed by fermenting for a period in the range of 60-120 hours. The media is stirred and aerated with 0.3-1 vvm air in order to obtain the fermentation broth.

c) The broth obtained in step (b) is separated using a vacuum drum filter.

Example 1

Materials

Wheat bran was obtained from VALSEMÆLLEN A/S (batch 113104),

Sugar beet pulp pellets obtained from the dried residuals from sugar production from sugar beets were obtained from Danisco Sugar A/S (batch 113117), Ammonium sulphate (No. 062174, DSM Fibre Intermediates standard product), Potassium nitrate (No. 002888, Brøste A/S standard product).

Fermentor:

Seed fermentor: 5 m$^3$ from Randers Rustfri Stålindustri A/S and stirrer from Lightning 155 rpm 9.5 kW Main fermentor: 50 m$^3$ from Randers Rustfri Stålindustri A/S and stirrer from Lightning 180 rpm 100 kW Vacuum drum filter: 24 m$^2$ filter from M&J Separation Division.

Membrane filter: Alfa Laval Nordic A/S type: Filter 517829 type GR70PE 6338/40

A seed culture of *Aspergillus tubingensis* 4M146 (CBS123488) was prepared in a 5 m$^3$ fermentor by inoculating the organism to the inoculation medium and incubating at 30±0.5° C., stirring and sterile air 0.5 vvm for 36 h. The specifically designed starting medium for the incubation contained:

| Ingrediens | Proportion kg |
|---|---|
| Wheat bran | 176 |
| Sugar beet pulp pellets | 177 |
| Ammonium sulfate | 16 |
| Potassium nitrate | 8 |
| Water | 3400 |

The fermentation medium was heated by the use of water steam whereby further 50-300 kg such as 100 kg water is added depending on the temperature of the starting medium.

The pH of the medium was controlled at 3.5 by addition of sulphuric acid and sodium hydroxide.

The specifically designed medium for fermentation was prepared in a 50 m$^3$ fermentor and contained:

| Ingrediens | Proportion kg |
|---|---|
| Wheat Bran | 1806 |
| Sugar beet pulp pellets | 1709 |
| Ammonium sulfate | 160 |
| Potassium nitrate | 80 |
| Water | 34000 |

The fermentation medium was heated by the use of water steam whereby further 400-8000 kg such as 2500 kg water is added depending on the temperature of the starting medium.

The medium was inoculated with the seed culture (10% v/v) at 30±0.5° C. with air supply at 0.5 vvm during stirring for 76 hours. The pH was controlled at 3.5 by addition of sulfuric acid and sodium hydroxide.

On completion of the fermentation, the broth was separated on a vacuum drum filter and the filtrate was concentrated on a membrane ultra filter by factor 15.

Example 2

A seed culture of *Aspergillus tubingensis* 4M146 (CBS123488) was prepared in a 5 m$^3$ fermentor by inoculation of the organism to the inoculation medium and incubating at 30±0.5° C. with stirring and an air supply of 0.5 vvm for 33 h. The specifically designed medium for incubating contained:

| Ingrediens | Proportion kg |
|---|---|
| Wheat Bran | 161 |
| Sugar beet pulp pellets | 167 |
| Ammonium sulfate | 16 |
| Potassium nitrate | 8 |
| Water | 3400 |

The fermentation medium was heated by the use of water steam whereby further 50-300 kg such as 100 kg water is added depending on the temperature of the starting medium.

The pH of the medium was controlled at 3.5 by addition of sulphuric acid and sodium hydroxide.

The specifically designed medium for fermentation prepared in a 50 m$^3$ fermentor contained:

| Ingrediens | Proportion kg |
|---|---|
| Wheat bran | 1806 |
| Sugar beet pulp pellets | 1612 |
| Ammonium sulfate | 160 |
| Potassium nitrate | 80 |
| Water | 34000 |

The fermentation medium was heated by the use of water steam whereby further 400-8000 kg such as 2500 kg water is added depending on the temperature of the starting medium.

The medium was inoculated with the seed culture (10% v/v) at 30±0.5° C., for 70 hours, with stirring and an air supply of 0.5 vvm.

The pH of the medium was controlled at 3.5 by addition of sulphuric acid and sodium hydroxide to the 50 m$^3$ fermentor On completion of the fermentation, the broth was separated on a vacuum drum filter and the filtrate was concentrated on a membrane ultra filter by factor 15.

Example 3

Fermentations were performed at different pH values in 5 m$^3$ fermentors (Randers Rustfri Stålindustri A/S). Fermentations were performed as described in example 2 adjusting pH with sulphuric acid and sodium hydroxide. At pH 3.5 two different strains were tested (*Aspergillus niger* 4M147)*. The activity of each batch was measured by assay 1, and Results are given in table 1.

TABLE 1 fermentation at different pH

| | Activity | | | Activity | |
|---|---|---|---|---|---|
| | Fermentation time | | | | |
| pH | (h) | Units/ml | Fermentation time (h) | Units/ml |
| 4.5 | 88 | 2.8 | 142 | 4.9 |
| 3.5 | 86 | 8.8 | 134 | 8.7 |
| 3.5* | 88 | 5.1 | 124 | 5.0 |
| 3.25 | 85 | 5.8 | 118 | 3.8 |
| 3.0 | 82 | 8.0 | ** | |

*A. niger 4M147.
** not measured

Example 4

Three independent fermentations were done as described in example 1 and the protein profile for the enzyme products were compared by chromatography.

Preparation of Pectinase samples, desalting on PD-10 column.

PD-10 columns were prepared as described by the manufacturer (Amersham Bio.) and equilibrated with 20 mM Tris/HCl buffer, pH 8.0 (buffer A). 2.5 ml of samples were desalted and kept at 5° C.

Characterization of Pectinase Samples on MonoQ Column

The column (MonoQ HR5/5) was prepared as described by the manufacturer (Amersham Bio.) and equilibrated with 20 mM Tris/HCl buffer, pH 8.0 (buffer A). The desalted sample (50 μl) was applied to the column at a flow rate of 1.5 ml/min. The column was washed with buffer A and the bound proteins were eluted with a liner gradient of 0-0.6 M NaCl in 20 mM Tris/HCl, pH 8.0

Absorption was normalized with activity. As determined by the viscometric QVC method (Assay 1).

Figure 4:
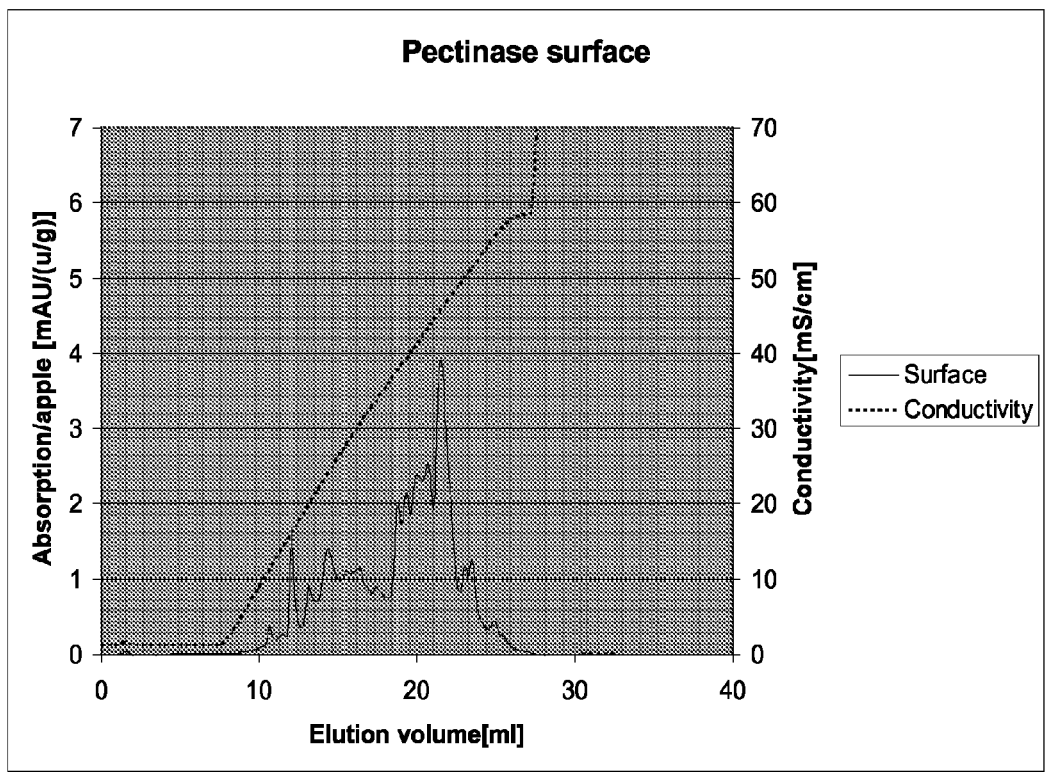
FIG. 4 shows the protein profile of an enzyme product from a fermentation using a surface fermentation method as described in example 4.
Figure 5:
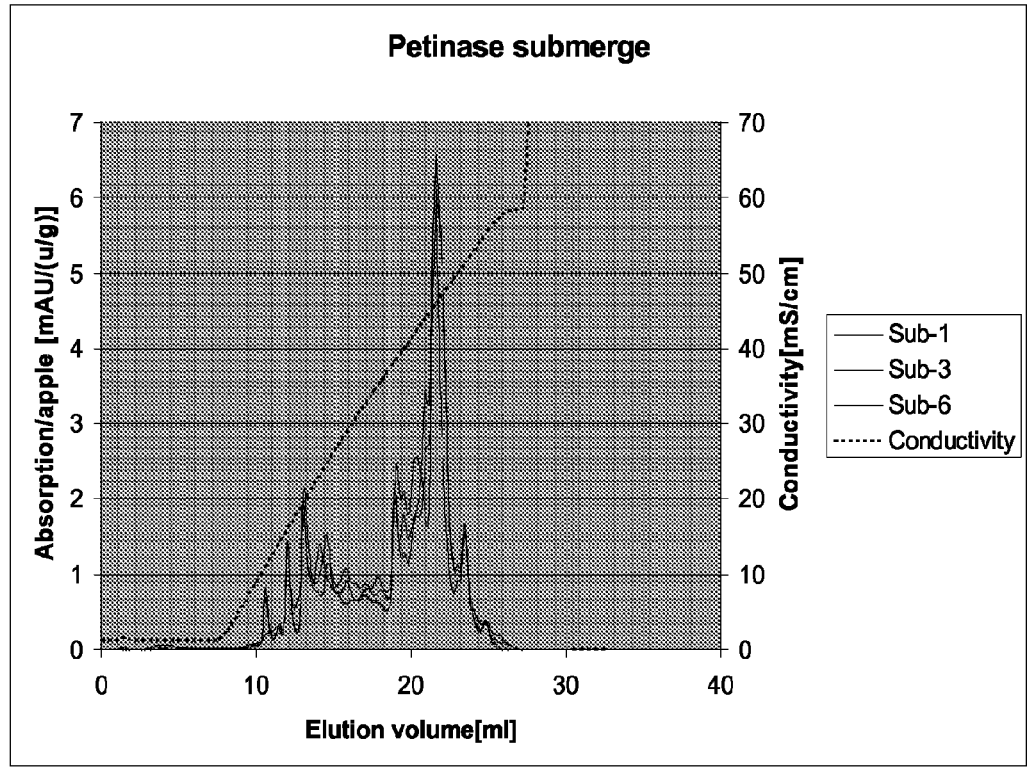
FIG. 5 shows the protein profile of enzyme products from 3 fermentations using the submerged fermentation method according to the invention as described in example 4.
Figure 6:
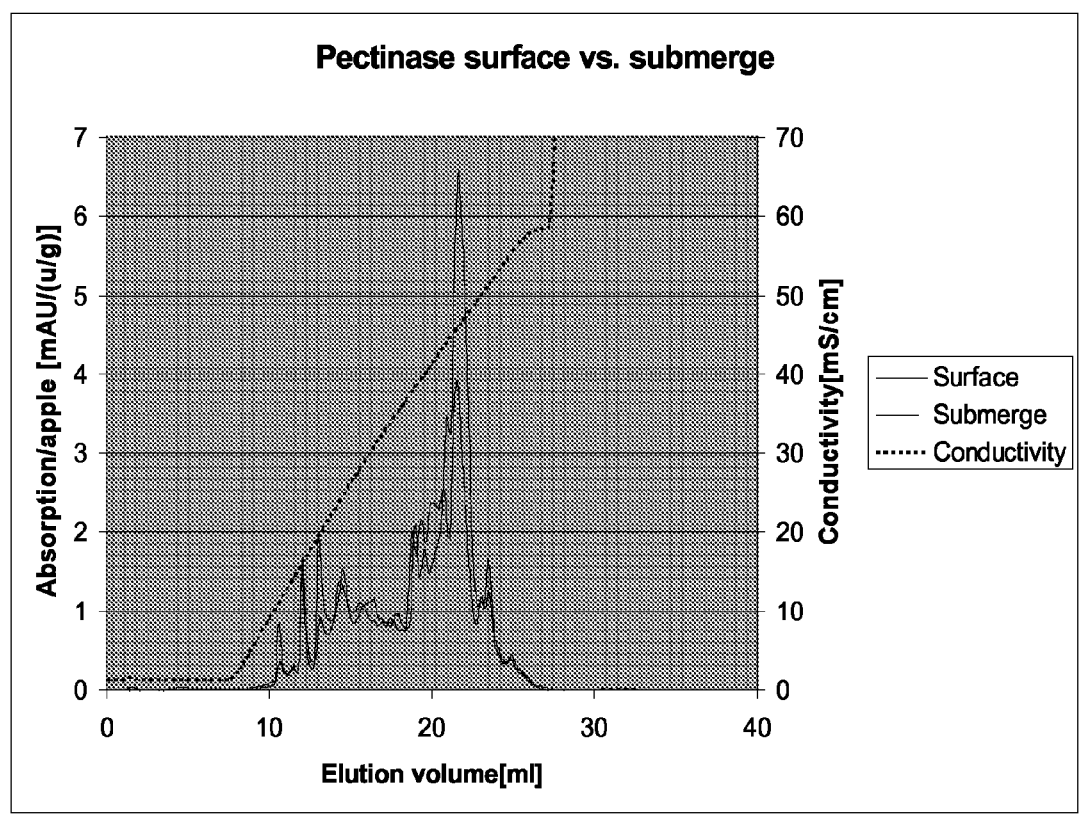
FIG. 6 shows a comparison of the protein profile of enzyme products from fermentations using the submerged fermentation method according to the invention and a surface fermentation method as described in example 4.

The protein profile of enzyme products from 3 different fermentations using submerged fermentation is shown in FIG. 5 and the protein profile of an enzyme product from a fermentation using surface fermentation is shown in FIG. 4. The protein profile of the surface fermentation is compared to the protein profile of the sub-merged fermentations are shown in FIG. 6.

Gel and protein data were used to qualify the three batches of concentrate produced using the submerged fermentation method. These samples were compared to a concentrate produced using a surface fermentation method.

Activity and Protein Data

| Description | Activity (U/mL) | Total Protein (mg/mL) | TCA Protein (mg/mL) | TCA/Total Protein % | Activity/TCA Protein (U/mg) |
|---|---|---|---|---|---|
| Surface Conc. (Control) | 240 | 88.93 | 54.40 | 61.17 | 4.42 |
| Submerged Conc. | 268 | 108.10 | 63.95 | 59.16 | 4.20 |
| Submerged Conc. | 199 | 62.94 | 39.75 | 63.16 | 5.01 |
| Submerged Conc. | 244 | 86.41 | 53.60 | 62.03 | 4.56 |

The samples were measured for TCA and Total protein by nitrogen analysis (with a conversion of 6.25 g protein/g nitrogen) as described in "Assay 15.b" described in the following.

Gel Data

The samples were prepped without TCA inactivation and loaded onto a SDS-NuPAGE gel based on equal activity using an estimated TCA protein/Activity value of 0.221 mg/U. The gel was set up in this manner:

| Lane | Description | Protein Load (μg) |
|---|---|---|
| 1 | | |
| 2 | Molecular Weight Marker | |
| 3 | Surface Conc. (Control) | 2.5 |
| 4 | Submerged Conc. | 2.5 |
| 5 | Submerged Conc. | 2.5 |
| 6 | Submerged Conc. | 2.5 |
| 7 | Molecular Weight Marker | |
| 8 | Surface Conc. (Control) | 5 |
| 9 | Submerged Conc. | 5 |
| 10 | Submerged Conc. | 5 |
| 11 | Submerged Conc. | 5 |

Results

Figure 7:
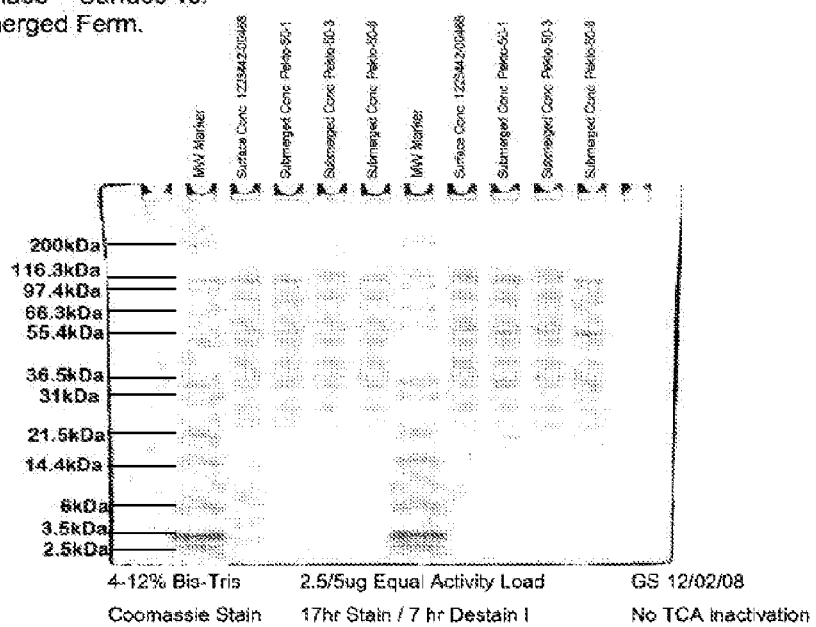
FIG. 7 shows the gel scan prepared in example 4.

The tca/total protein and activity/tca protein ratios are similar for all the samples. The gel shows that the 3 batches of submerged fermentation samples have a similar band pattern. The fermentation strain produces multiple enzymes and there is not a single active band, but rather multiple active bands. The gel scan is shown in FIG. 7.

Example 5

The concentrated filtrate of example two was measured in the following assays 1-3 and 5-15 and the results is given in below table.

| Assay | pH | Temperature (deg C.) | Cell free fermentation concentrated supernatant from submerged fermentation | Assay |
|---|---|---|---|---|
| QVC assay | | | 177 | Assay 1 |
| AJDU | 3.5 | 55 | 152.3 | Assay 2 |
| | | | | Apple Juice Depectinization Units (AJDU) |

| Assay | pH | Temperature (deg C.) | Cell free fermentation concentrated supernatant from submerged fermentation | Assay |
|---|---|---|---|---|
| Pectin lyase | 3.5 | 55 | 521.4 | Assay 3 Pectin transeliminase (Apple pectin trans-elimination method) |
| Polygalacturonase | 3.5 | 50 | 8353 | Assay 5. Polygalacturonase activity |
| Polygalacturonase | 3.5 | 30 | 2297 | Assay 6. Polygalacturonase (viscometric PGA method: microviscometer) |
| Pectinesterase | 3.6-4.6 | 50 | 2245-1283 | Assay 7. Pectinesterase (Titrative pectin method) |
| Arabinanase | 3.5 | 50 | 1332 | Assay 8. |
| Cellulase | 3.5 | 50 | 908 | Assay 9. Cellulase (DNS CMC method) |
| Cellulase | 5.0 | 50 | 829 | Assay 9. Cellulase (DNS CMC method) |
| 1,3-β-glucanase | 5.0 | 50 | 129 | Assay 10. Laminarinase (DNS laminarin method) |
| Endo-1,4-β-xylanase | 3.5 | 50 | 3353 | Assay 11. Endo-1,4-β-xylanase (DNS birchwood xylan method) |
| Endo-1,4-β-xylanase | 5.0 | 50 | 2633 | Assay 11. Endo-1,4-β-xylanase (DNS birchwood xylan method) |
| α-amylase | 5.4 | 40 | 5.0 | Assay 12. α-Amylase (fungal) (Ceralpha method for fungal α-amylase using Amylase HR reagent) |
| α-holoamylase | 3.8 | 60 | 6.0 | Assay 13. Alpha-Holoamylase Enzyme Activity [WKI-QC-050-01] |
| Glucoamylase (C100-02) | 4.3 | 30 | <25 | Assay 14 |
| Protein concentration (BCA) | | | 94.1 | Assay 15a |

Please note that many of the enzyme activities are measured at experimental conditions such as temperature and pH close to "real life conditions" in fruit/and wine applications, such as pH as low as 3.5 and temperatures as high as 60° C.

Example 6

| Assay | pH | Temp (° C.) | Batch 1 | Batch 2 | Batch 3 | Batch 4 | Batch 5 | Batch 6 |
|---|---|---|---|---|---|---|---|---|
| Assay 3 (Pectin lyase) | 3.5 | 55 | 425.6 | 308.1 | 322.3 | 370.0 | 292.5 | 334.2 |
| Assay 5 (Polygalacturonase) | 3.5 | 50 | 7436 | 3538 | 4933 | 4514 | 5331 | 5433 |
| Assay 6 (Polygalacturonase) | 3.5 | 30 | 1673 | 1098 | 1145 | 916 | 876 | 1159 |
| Assay 8 (Arabinanase) | 3.5 | 50 | 990 | 562 | 584 | 620 | 579 | 648 |
| Assay 9 (Cellulase) | 3.5 | 50 | 1084 | 715 | 576 | 710 | 549 | 645 |
| Assay 10 (1,3-β-glucanase) | 3.5 | 50 | 69 | 30 | 33 | 44 | 36 | 32 |
| Assay 11 (Endo-1,4-β-xylanase) | 3.5 | 50 | 3379 | 2657 | 2063 | 2561 | 1773 | 2366 |
| Assay 12 (α-amylase) | 5.4 | 40 | 4.8 | 2.0 | 2.4 | 3.7 | 2.8 | 2.4 |
| Assay 13 (α-holoamylase) | 3.8 | 60 | 6.3 | 3.7 | 4.3 | 4.8 | 3.9 | 4.2 |
| Assay 14 (Glucoamylase) | 4.3 | 30 | 10.4 | 6.8 | 7.8 | 7.7 | 8.7 | 8.5 |
| Assay 15 a Protein concentration (BCA) | | | 92.0 | 51.0 | 54.7 | 70.0 | 55.0 | 60.7 |

Six different fermentations were performed as described in example 1. The enzyme activities determined in the concentrated ferment for the different batches of the enzyme product are shown in above table measured according to the same assays as described in example 5.

Example 6

Figure 8:
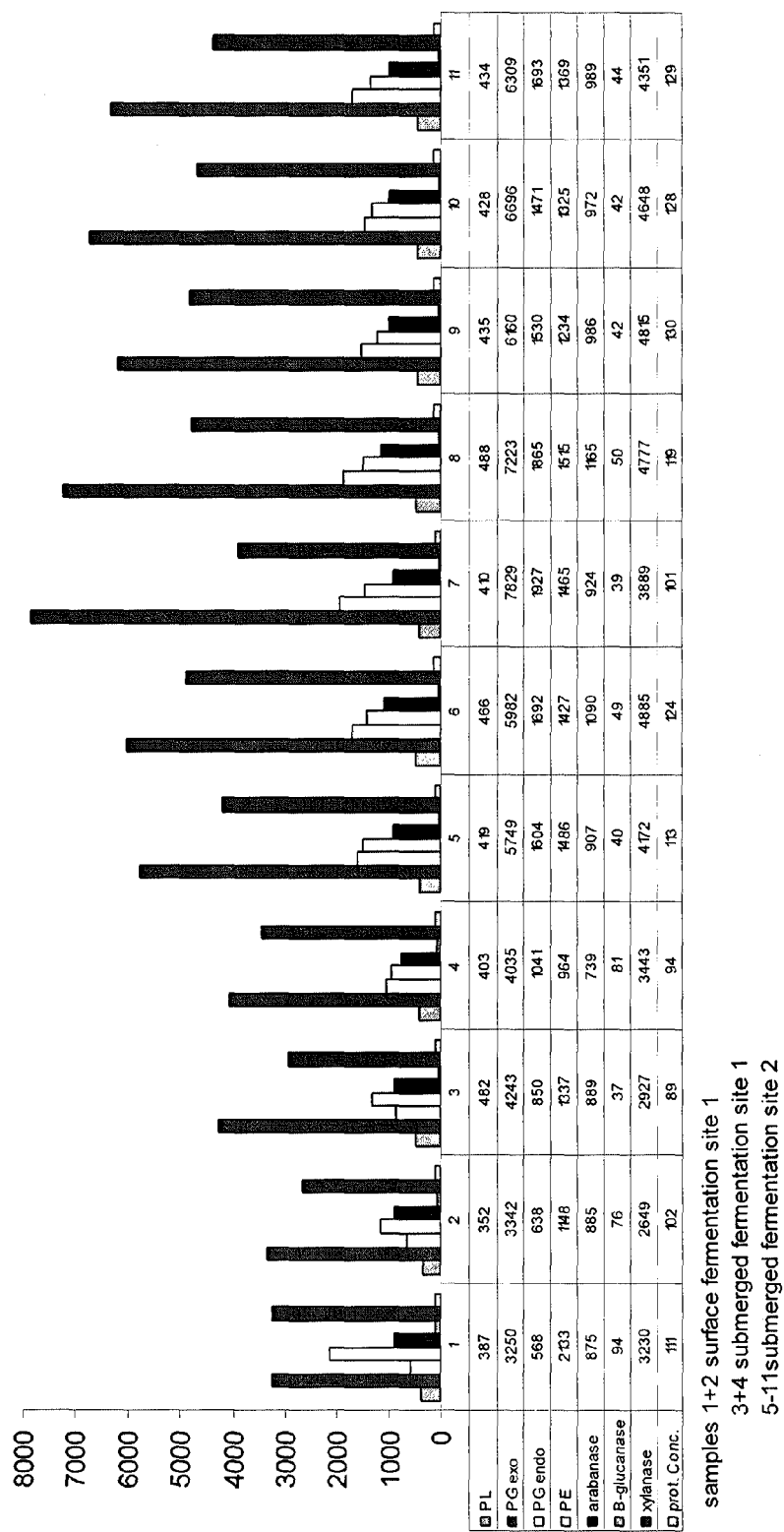
FIG. 8 shows the enzymatic activities of concentrated enzyme products obtained at two surface fermentations at site 1 (sample 1-2) and 2 submerged fermentations at site 1 (sample 3-4) and 7 submerged fermentations at site 2 (sample 5-11). Enzyme activities expressed according to units of the corresponding assay as described in Example 5.

Nine different fermentations (fermentation 3-11) were performed as described in example 1 by submerged fermentation at to different production sites (Site 1 and Site 2). The enzyme activities determined in the concentrated ferment for the different batches of the enzyme product are shown in FIG. 8 and are measured according to the same assays as described in example 5. Two different fermentations (fermentation 1-2) were performed by surface fermentation with the same medium as used for the submerged fermentations, and the enzyme activities were measured as for the submerged fermentations.

Assays

Assay 1: QVC Viscometric Activity Determination

Method

The enzyme is added to a known amount of apple juice at a known pH, temperature and time, followed by pasteurisation. As standard pH 3.75, 50° C. and a reaction time of 60 min is used if no other parameters are given. After filtration viscosity is determined by the running time from a pipette. Activity is determined by comparing to the run time for a standard enzyme with known activity.

Juice is made from apples; Golden delicious (50%), Cox Orange (25%) and Lobo (25%) and pasteurised (95° C., 3 min). Before the assay pH is adjusted to pH 3.75 (HCl or NaOH). The run time for the juice is to be at least 50 sek.

The enzyme standard is prepared from Pectozyme Power-Mash (Danisco 1247062) as an average of 30 products with known activity. This mixture from 30 products is used as standard.

Juice and enzyme is mixed and incubated at 50° C. for 60 min before determination of run time (in doublets). Pure juice and completely hydrolysed juice are also included in the test. Completely hydrolysed juice is made by addition of 2 ml un-diluted Pectozyme PowerMash to 25 ml juice and incubated for 60 min at 50° C.

The pipette used needs to have a run time of 20-21 sec. when using water at 25° C.

All enzyme samples are incubated with the juice for 60 min at 50° C. followed by a heat treatment in boiling water for 5 min.

The samples are cooled down to 25° C. and filtered. The temperature of the samples is stabilized at 25.0° C. before the run time is determined by the pipette.

A standard curve is made from the run time obtained with juice mixed with the standard enzyme solution in known concentrations (obtained by dilution of the standard). The standard curve is made as a correlation between activity and run time.

The activity of the enzyme is then found from the correlation of the run time with the activity.

According to an aspect/embodiment, the enzyme product is standardized according to its QVC Viscometric activity.

Assay 2. Apple Juice Depectinization Units (AJDU)

Principle

This assay is based on the time required to depectinize a single strength, unclarified, apple juice substrate at pH 3.5 and 55° C. The end point is determined by isopropanol precipitation of pectin. Apple Juice Depectinization Units (AJDU) is determined by correlating the depectinization time of the unknown sample to the depectinization time of an enzyme standard of known activity under the conditions of the assay.

Reagents Required

D,L-Malic acid ($C_4H_6O_5$), ≥99.5%. Supplier: Merck Ltd Product no.: 1003820250. M.W.: 134.09 g/mol.

Sodium hydroxide (NaOH), 'AnalaR'. Supplier: Merck Ltd (BDH) Product no. 10252. M.W.: 40.00 g/mol.

Isopropanol ($C_3H_8O$), 'Rectapur'. Supplier: Merck Ltd (BDH) Product no.: 20 839.322. M.W.: 60.10 g/mol.

Enzyme reference standard: Enzyme of known AJDU activity.

Preparation of Apple Juice Solution

The pH of unclarified apple juice was adjusted to pH 3.50 with D,L-malic acid or sodium hydroxide (10% w/v) and filtered (Buckner funnel, glass micro-fibre GF/A filters.

Procedure

Five dilutions of the enzyme reference standard were prepared for the standard curve. Each of the final solutions will reach end points in no less than 90 minutes and no more than 150 minutes. The enzyme product was diluted in water to a concentration giving an end point between 100 minutes and 140 minutes under the conditions of the assay.

2.0 ml of isopropyl alcohol was added to into the test tubes. After 90 minutes, 1.0 ml aliquot from the reaction tube transferred to tubes containing isopropyl alcohol. Mix gently and after 2 min the tubes were evaluated. If the reaction end point has not been reached, a pectin precipitate will appear as anything from fine particles to a viscous gel, depending on the degree of depectinization (vide supra). The absence of precipitate after two minutes means that the reaction end point has been reached. The reaction end point must be reached between 100 and 150 minutes. The assay was repeated with adjusted enzyme dilutions until the reaction time was inside this range.

Calculation

Apple Juice Depectinization Units (AJDU/ml) are determined by correlating depectinization time of the unknown sample with that of a pectinase standard of known activity using a defined single strength apple juice substrate.

A standard curve as shown in FIG. 1 was made by plotting the concentrations of the diluted enzyme standard solutions in AJDU/1000 l along the x-axis and the corresponding end points in minutes along the y-axis.

Using AJDU/ml for the x-values and end point for the y-values, the following slope and y-intercept values are obtained by the particular standard:

$$m=-152694; i=249.21$$

The calculation of the AJDU was done by the formula below. E.g. as an example if the enzyme product was diluted to a concentration of 0.000004599 g/ml. The end point was 130 min.

$$AJDU/g = \frac{130 - 249.21}{-152694 \times 0.000004599} = \underline{167.2}$$

All results are limited to one digit by the accuracy of the end point.

Assay 3. Pectin Transeliminase (Apple Pectin Trans-Elimination Method)

Principle

The assay of pectin transeliminase (pectin lyase, EC 4.2.2.10) is based on the enzymatic hydrolysis of internal α-1,4 bonds between galacturonic acid residues in an apple pectin substrate. The progress increase in 4,5-unsaturated oligogalacturonates was followed by an increase in absorbance using a spectrophotometer at 238 nm. Enzyme activity is calculated from the increase in absorbance at 238 nm per unit time.

The standard assay was carried out at pH 3.5 and 30° C., it can be performed at different pH and temperature values for the additional characterisation and specification of enzymes.

Unit Definition

One unit of pectin transeliminase activity is defined as the amount of enzyme product (normalised for total assay volume) that gives an increase in $\Delta OD_{238\,nm} \cdot min^{-1}$ under the conditions of the assay (pH 3.5 and 30° C.).

Materials

NYL Filter Unit—75 mm Ø, 500 ml, 0.45 μm (Nalgene), vacuum pump; or, alternatively for smaller substrate volumes syringe 50 ml, Syringe filters GD/X—0.45 μm, (Whatman)

Pectin (apple). Supplier: Herbstreith & Fox KG. Product no.: Classic AU 202 (68-76% esterification).

Citric acid anhydrous fine-granular extra pure ($C_6H_8O_7$). Supplier: VWR International Ltd (Merck Ltd). Product no.: 1002474. M.W.: 192.13.

Sodium hydroxide (NaOH) 0.1 mol/l (0.1 N), 'Titrisol®'. Supplier: VWR International Ltd (Merck Ltd). Product no.: 109956.

Hydrochloric acid (HCl) 0.1 mol/l (0.1 N), 'Titrisol®'. Supplier: VWR International Ltd (Merck Ltd). Product no.: 109973.

Enzyme reference standard, which is an Enzyme of known activity

The volumes of reagents given are examples. Different volumes can be prepared as required. Water quality is glass distilled water or equivalent.

Reagents:
1. 0.1 M sodium citrate/HCl buffer, pH 3.5
2. 0.333%(w/v solution in buffer) Pectin solution (substrate solution)
3. Dilutions of the enzyme product in buffer.

Further dilutions were made until the resulting $\Delta OD_{238\,nm}$ was in the range 0.030-0.035 to keep the reaction rate linear over the time of the assay.

Procedure

Enzyme product and substrate is mixed and $\Delta OD_{238\,nm}$ was followed by a kinetic program. If $\Delta OD_{238\,nm}$ was measured out-side the range 0.030-0.035, then the assay was repeated with a more appropriate enzyme dilution.

All assays were done at least in duplicate.

Calculation

1. Determine $\Delta OD_{238\,nm}$ per minute from the spectrophotometer kinetic program.
2. The activity is calculated as follows:

$$\text{Activity}\,(u \cdot g^{-1}) = E \times A \times \frac{1}{V} \times \frac{D}{W}$$

where:
$E = \Delta OD_{238\,nm}$ per minute (average of 2 valid measurements)
A=total assay volume in ml
V=enzyme volume in ml
W=weight of enzyme in g used to make up diluted enzyme sample
D=cumulative dilution factor Assay 4. Rhamnogalacturonase Activity Assay For the isolation of modified hairy regions, Golden Delicious apples (10 kg) are crushed in a Magimix Cuisine Systeme 3000 and treated with an enzyme preparation (Biopectinase 200 L 0.05%) from Quest International for 4 hours at 55.degree. C. After centrifugation (Sorvall RC-5B) at 8000 g for 30 minutes the supernatant are ultrafiltered and concentrated in a Pellicon microfiltration unit having a molecular weight cut off of 50.000. The residue is dialysed and lyophilized.

The isolated polysaccharide is characterised by analyzing enzymatic degradation products. 5 ml of 0.2% solutions of the isolated Modified Hairy Regions in 0.05 M sodium acetate buffer (pH=5.0) are incubated with 10 mu.l enzyme preparations for 2 hours at 50 degree C. Analysis of the formed products is performed on a Dionex BioLC/HPAE chromatography system or by measuring the increase in the reducing end-groups making use of the DNS method. The Dionex system uses a Carbo Pac PA-1 anion exchange column (25 cm, 4 mmi.d.) and a CarboPac PA-1 Guard. The column was loaded with 25 .mu.l of the solution (0.2%) and eluted with a linear gradient of 0-0.5 M NaOAc in 0.1 N NaOH during 50 minutes. The flow rate was 1.0 ml/min and the process was monitored using a PE detector.

For the reducing end group method the DNS reagent was prepared as follows: 20.0 grams of 2-hydroxy-3,5 dinitrobenzoic acid (Merck 800141) is suspended in 400 ml distilled water. With continuous magnetic stirring, 300 ml of NaOH solution (32 grams in 300 ml distilled water) is gradually added to this suspension. The solution is warmed cautiously to 45 degree. C. until it was clear. Rochelle salt (600 g, K—Na-tartrate, Merck 8087) is added under continuous stirring. The solution is diluted to 2000 ml with distilled water and stored in a dark bottle at room temperature. Using the DNS method, 0.5 ml of the reaction mixture (MHR and enzyme preparation after 2 hours of incubation as described above), is added to 1.5 ml demi-water and 2 ml DNS-solution. The solution is boiled for 10 minutes and after cooling to room temperature the extinction is measured at 543 nm.

Assay 5. Polygalacturonase Activity Assay

Principle

The assay of polygalacturonase is based on colourimetrically determination of α-1,4 galacturonic acid oligosaccharides, by measuring increase in reducing groups using a 3,5-dinitrosalicylic acid reagent. Enzyme activity is calculated from the relationship between the concentration of reducing groups, as D-galacturonic acid.$H_2O$ equivalents, and absorbance at 540 nm.

The standard assay was carried out at pH 3.5, but can be performed at different pH values for the additional characterisation and specification of enzymes.

Unit Definition

One unit of polygalacturonase activity is defined as the amount of enzyme which produces 1μ mole D-galacturonic acid equivalents per minute under the conditions of the assay (pH 3.5 (or as specified) and 50° C.).

Materials

Polygalacturonic acid (BioChemika, ~95% (enzymatic)). Supplier: Sigma-Aldrich. Product no.: 81325.

D-(+)-Galacturonic acid monohydrate (BioChemika, ≥97.0%). Supplier: Sigma-Aldrich. Product no.: 48280. M.W.: 212.15.

Sodium acetate anhydrous 'AnalaR'. Supplier: Merck Ltd (BDH). Product no.: 10236. M.W.: 82.03.

Acetic acid ("glacial") 'AnalaR'. Supplier: Merck Ltd (BDH). Product no.: 10001. M.W.: 60.05.

3,5-Dinitrosalicylic acid GPR (3,5-dinitro-2-hydroxybenzoic acid). Supplier: Merck Ltd (BDH). Product no.: 28235.

Sodium hydroxide pellets 'AnalaR'. Supplier: Merck Ltd (BDH). Product no.: 10252. M.W.: 40.00.

Potassium sodium (+)-tartrate 'AnalaR'. Supplier: Merck Ltd (BDH). Product no.: 10219. M.W.: 282.22.

1.4%(w/v solution in 1M sodium acetate buffer pH 3.5) polygalacturonic acid (PGA) solution (substrate solution)

3,5-Dinitrosalicylic acid (DNS) solution in sodium hydroxide pellet (32 g/L)/potassium sodium tartate (600 g/L) buffer 0.10M Sodium acetate buffer, pH 3.5

D-Galacturonic acid standard solution (0.60 mg/ml)

Procedure

A D-galacturonic acid.$H_2O$ standard curve is made using 0, 0.015, 0.3, 0.45, 0.6 mg/ml of D-galacturonic acid.$H_2O$. DNS is added in the same amount as in the enzyme evaluation.

The enzyme product is mixed with the substrate solution (10 min at 50° C.) and the reaction stopped by addition of DNS solution and incubated at 95° C. for 5 min. The optical density is measured at 540 nm ($OD_{540\ nm}$).

The assay is non-linear with respect to correlation between substrate concentration and time.

Calculation

The exo-polygalacturonase activity is calculated as follows:

$$\text{Activity}\ (u \cdot ml^{-1}\ \text{or}\ u \cdot g^{-1}) = \frac{T-c}{m} \times A \times \frac{1}{212.15} \times 10^3 \times \frac{1}{V} \times \frac{1}{t} \times D$$

where:

$$T = \Delta OD_{540nm}\ \text{TEST}$$
$$= OD_{540nm}\ \text{TEST} - OD_{540nm}\ \text{BLANK}$$

m=gradient of the standard curve (approximately 1.0)
c=y axis intercept of the standard curve
212.15=molecular weight of D-galacturonic acid.$H_2O$
$10^3$=to convert to µmoles
A=assay volume in ml
V=enzyme volume in ml
t=assay time in minutes
D=actual enzyme dilution factor (e.g. for 1.000 g diluted to 1 liter D=1000)

Assay 6. Polygalacturonase (viscometric PGA method: Microviscometer) Assay

Principle

Enzyme activity is measured by the rate of reduction in relative viscosity of the polygalacturonic acid solution. The assay was carried out at pH 3.5 and 30° C., it can be performed at different pH values and temperatures for the additional characterisation and specification of enzymes.

Unit Definition

One unit of polygalacturonase activity is defined as the amount of enzyme which will hydrolyse the substrate, reducing the viscosity of the solution, to give a change in relative fluidity of 1 dimensionless unit per minute under the conditions of the assay (pH 3.5 (or as specified) and 30° C. (or as specified)).

Materials

Microviscometer (e.g. Haake microviscometer or Rhovisc microviscometer) and operating software Ultrasonic water bath Polygalacturonic acid (BioChemika, ~95% (enzymatic)). Supplier: Sigma-Aldrich. Product no.: 81325 tri-Sodium phosphate dodecahydrate 'GR for analysis'. Supplier: Merck Chemicals (VWR). Product no.: 106572. M.W.: 380.18

Citric acid monohydrate 'GR for analysis'. Supplier: Merck Chemicals (VWR). Product no.: 100244. M.W.: 210.14

Acetone 'GR for analysis'. Supplier: Merck Chemicals (VWR). Product no.: 100014. M.W.: 58.08

Sterile Glassware and Water was Used 1.4%(w/v solution of polygalacturonic acid (PGA) in tri-Sodium phosphate dodecahydrate buffer (1 g/100 ml)) adjusted if necessay to pH 3.5 with sterile 1.90%(w/v) citric acid solution (substrate solution)

1.0 M Sodium hydroxide solution 1.90% solution of citric acid monohydrate (sterile)

Calibration of the Microviscometer

Microviscometer was calibrated both at start and end of the measurements against both a water blank and substrate solution (substrate blank).

Enzyme dilutions of the enzyme product was prepared to give:

$$\frac{\Delta(\text{drop time})}{\Delta t} = -50 \pm 5\ \text{ms} \cdot \text{min}^{-1}$$

over 5-15 minute measurement period of the assay (corresponding to a total Δ(drop time) of 450-550 ms over the 10 minute measurement period). Assay results, over a period of time, should give an average Δ(drop time)/Δt of 50 ms·min$^{-1}$, and not be biased towards the extreme values of the acceptable range. A further, and necessary, check is that the diluted enzyme solution should give a SLOPE (change in relative fluidity per minute) in the range of 0.010-0.020.

Procedure

Using the same volume of 1.40%(w/v solution) polygalacturonic acid solution determined in the calibration of the substrate blank, an assay solution was prepared comprising 2.20 ml 1.40%(w/v solution) polygalacturonic acid solution, pH 3.5 and 2.50 ml sterile glass distilled water.

A calibrated gold ball (0.1-2 mPa·s) was placed into a clean dry sample syringe and a Teflon™ seal plunger was inserted behind the ball.

The diluted enzyme solution was added to the substrate assay solution at 30° C. The assay solution was inserted by syringe into the microviscometer exactly after 60 seconds. The microviscometer will measures test efflux times ($T_t$) every 30 seconds. After 15 minutes the assay will terminate. To obtain a SLOPE within the range of 0.010-0.020, the total reduction in test efflux ($T_t$) over the 10 minute period from 5-15 minutes will be in the region of 450-550 ms.

Calculation $F_r$=relative fluidity
$T_w$=water efflux time (ms)
$T_s$=substrate efflux time (ms)
$T_t$=test efflux time (ms) at time t
t=assay time (minutes)
$t_{1/2}$=assay time (t) minus ½ the test efflux time ($T_t$)) (minutes)
DF=dilution factor (e.g. for 1 g diluted to 100 ml, then 1 ml of this solution diluted to 200 ml gives DF=20000)
S=total volume of test (ml)
V=volume of enzyme solution in test (0.30 ml)

$F_r$ values for each of the test efflux times ($T_t$) were calculated and plotted against $t_{1/2}$. The SLOPE (change in relative fluidity per minute) of the straight line was determined by performing regression analysis to obtain the straight line of best fit (the regression coefficient ($R^2$) is a measure of the goodness of fit).The SLOPE is proportional to the enzyme activity. (The slope of a series of experimental points, i.e. at different assay times, is a more accurate measurement of endo-activity than that derived from a single calculation of one $F_r$.)

$$\text{Activity }(u\cdot ml^{-1} \text{ or } u\cdot gl^{-1}) = \text{SLOPE} \times \text{DF} \times (5/V)$$

Assay 7. Pectinesterase (Titrative Pectin Method)

Principle

The assay of pectinesterase is based on the enzymatic hydrolysis of the methyl ester bond in a high ester pectin (apple pectin with 68-76% degree of esterification). The pH of the reaction is kept constant by alkalimetric titration neutralising the "liberated" galaturonic acid groups. The $pK_a$ of galacturonic acid is approximately 3.5 at 30° C. in aqueous solution, so the $pK_a$ for polygalacturonic acid is taken as being similar. The activity was measured by alkalimetric titration. The assay was carried out at pH 4.6 and 30° C. but it can be performed at different values for the additional characterisation and specification of enzymes.

Unit Definition

One unit of pectinesterase activity is defined as the amount of enzyme that catalyses the hydrolysis of 1 μmole of methyl ester bonds (releasing 1 μmole pectic acid) per minute under the conditions of the assay (pH 4.6 and 30° C.) or as specified.

Materials

Pectin (apple). Supplier: Herbstreith & Fox KG. Product no.: Classic AU 202 (68-76% esterification).

Magnesium chloride hexahydrate 'GR for analysis'. Supplier: Merck Chemicals (VWR). Product no.:105833. M.W.: 203.30

Sodium hydroxide pellets 'GR for analysis'. Supplier Merck Chemicals (VWR). Product no.:106469. M.W.: 40.00

0.50%(w/v) solution) apple pectin with 10 mM $MgCl_2.6H_2O$, pH 4.6 (substrate solution)

0.020 M Sodium hydroxide solution

Dilutions of the enzyme product.

Procedure

The enzyme dilution was added to the apple pectin substrate solution (30° C., pH 4.60) using an automatic pH stat titrator to keep the pH at pH 4.6 (0.020 M sodium hydroxide solution). The consumption of the 0.020 M sodium hydroxide solution over 5 minutes was recorded; however, the consumption over the time period of 2.0-4.0 only was used in the calculation. The response over the 5 minute reaction period is used to check the linearity of the reaction rate.

Calculation

The activity is calculated as follows:

$$\text{Activity }(u \cdot ml^{-1} \text{ or } u \cdot g^{-1}) = \frac{T}{(C \times 10^3)} \times \frac{1}{t} \times \frac{1}{V} \times \frac{D}{W} \times [1 + 10^{(pK_a - pH)}]$$

where:

T=volume of 0.020 M sodium hydroxide solution added between 2.0-4.0 minutes (ml)

C=concentration of sodium hydroxide solution (M)

$10^3$=to convert to from volume titrated in ml and to μmoles t=assay time (minutes)

V=volume of diluted enzyme in assay (ml)

W=weight or volume of undiluted enzyme diluted (g or ml)

D=enzyme dilution factor (i.e. the amount the undiluted enzyme is diluted)

$pK_a = pK_a$ of polygalacturonic acid pH=assay, and control, pH

Assay 8. Arabinanase Assay.

Principle

The assay of arabinanase activity is based on colorimetrically determination by measuring the resulting increase in reducing groups using a 3,5-dinitrosalicylic acid reagent. Enzyme activity was calculated from the relationship between the concentration of reducing groups, as arabinoase equivalents, and absorbance at 540 nm.

The assay was carried out at pH 3.5, but it can be performed at different pH values for the additional characterisation and specification of enzymes.

Unit Definition

One unit of arabinanase (Arabinanase (endo-1,5-alpha-L-arabinanase)) activity is defined as the amount of enzyme which produces 1 μmole arabinoase equivalents per minute under the conditions of the assay (pH 3.5 (or as specified) and 50° C.).

Materials

Megazyme Sugar Beet Arabinan

Arabinose Sigma A3131 M.W.: 150.1

Sodium acetate anhydrous 'AnalaR'. Supplier: Merck Ltd (BDH). Product no.: 10236. M.W.: 82.03

Acetic acid ("glacial") 'AnalaR'. Supplier: Merck Ltd (BDH). Product no.: 10001. M.W.: 60.05

3,5-Dinitrosalicylic acid GPR (3,5-dinitro-2-hydroxybenzoic acid). Supplier: Merck Ltd (BDH). Product no.: 28235

Sodium hydroxide pellets 'AnalaR'. Supplier: Merck Ltd (BDH). Product no.: 10252. M.W.: 40.00

Potassium sodium (+)-tartrate 'AnalR'. Supplier: Merck Ltd (BDH). Product no.: 10219. M.W.: 282.22

1.5%(w/v solution) Arabinan solution in 0.1M sodium acetate buffer, pH 3.5 (substrate solution).

3,5-Dinitrosalicylic acid (DNS) solution. 20 g/L of DNS in buffer containing 32 g/L sodium hydroxide pellets, and 600 g/L potassium sodium (+)-tartrate.

Arabinoase standard solution (0.50 mg/ml)

Procedure

The enzyme product was diluted into samples and a glucose standard curve was made using arabinoase concentrations of 0, 0.125, 0.25, 0.375, and 0.5 mg/ml.

0.25 ml of enzyme solution was mixed with 1.75 ml of the substrate solution (1.5% w/v) at 50° C. and the reaction was stopped after 10 min by addition of DNS solution. Followed by heating to 95° C. for 5 minutes.

The optical density was measured at 540 nm ($OD_{540\,nm}$) of the different samples.

Calculation

Figure 2:
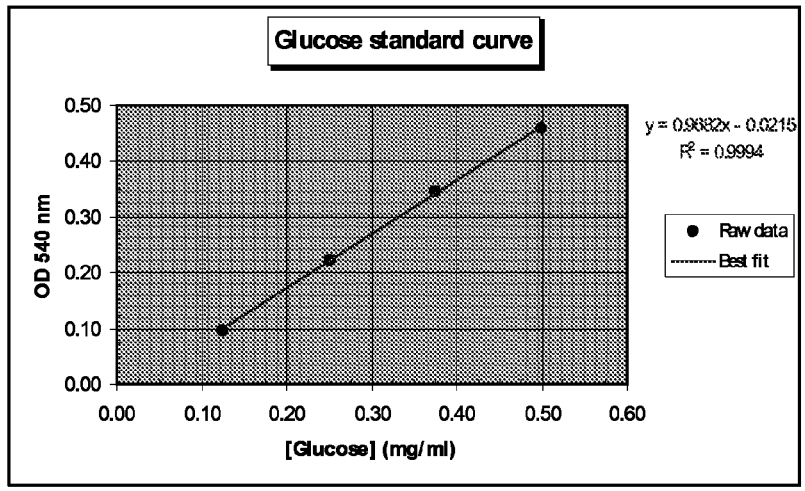
FIG. 2 shows a glucose standard curve made as described in "Assay 9" in the following under the heading "Assays".

The enzyme activity is determined from the standard curve as shown in FIG. 2.

The activity is calculated as follows:

$$\text{Activity }(u \cdot ml^{-1} \text{ or } u \cdot g^{-1}) = \frac{T-c}{m} \times A \times \frac{1}{150.13} \times 10^3 \times \frac{1}{V} \times \frac{1}{t} \times D$$

where:

$T = \Delta OD_{540nm}$ TEST $= OD_{540nm}$ TEST $- OD_{540nm}$ BLANK m=gradient of the standard curve (approximately 1.0)

c=y axis intercept of the standard curve (always negative and approximately −0.02)

150.13=molecular weight of arabinoase
$10^3$=to convert to μmoles
A=assay volume in ml
V=enzyme volume in ml
t=assay time in minutes
D=actual enzyme dilution factor (e.g. for 1.000 g diluted to 1 liter D=1000)

Assay 9. Cellulase (DNS CMC Method) Assay

Principle

The assay of cellulase is based on the enzymatic endohydrolysis of the 1,4-β-D-glucosidic bonds in carboxymethylcellulose (CMC), a β-1,4-glucan. The products of the reaction (β-1,4 glucan oligosaccharides) was determined colorimetrically by measuring the resulting increase in reducing groups using a 3,5-dinitrosalicylic acid reagent. Enzyme activity was calculated from the relationship between the concentration of reducing groups, as glucose equivalents, and absorbance at 540 nm.

The assay was carried out at pH 5.0, but it can be performed at different pH values for the additional characterisation and specification of enzymes.

Unit Definition

One unit of cellulase activity is defined as the amount of enzyme which produces 1 μmole glucose equivalents per minute under the conditions of the assay (pH 5.0 (or as specified) and 50° C.).

Materials

Carboxymethylcellulose. Supplier: Megazyme Ltd. Product no.: CM-Cellulose 4M

D-Glucose 'AnalaR'. Supplier: Merck Ltd (BDH). Product no.: 10117. M.W.: 180.16

Sodium acetate anhydrous 'AnalaR'. Supplier: Merck Ltd (BDH). Product no.: 10236. M.W.: 82.03

Acetic acid ("glacial") 'AnalaR'. Supplier: Merck Ltd (BDH). Product no.: 10001. M.W.: 60.05

3,5-Dinitrosalicylic acid GPR (3,5-dinitro-2-hydroxybenzoic acid). Supplier: Merck Ltd (BDH). Product no.: 28235

Sodium hydroxide pellets 'AnalaR'. Supplier: Merck Ltd (BDH). Product no.: 10252. M.W.: 40.00

Potassium sodium (+)-tartrate 'AnalaR'. Supplier: Merck Ltd (BDH). Product no.: 10219. M.W.: 282.22

1.5%(w/v) solution) Carboxymethylcellulose (CMC) solution in 0.1M sodium acetate buffer, pH 5.0 (substrate solution).

3,5-Dinitrosalicylic acid (DNS) solution. 20 g/L of DNS in buffer containing 32 g/L sodium hydroxide pellets, and 600 g/L potassium sodium (+)-tartrate.

Glucose standard solution (0.50 mg/ml)

Procedure

The enzyme product was diluted into samples and a glucose standard curve as shown in FIG. 2 was made using glucose concentrations of 0, 0.125, 0.25, 0.375, and 0.5 mg/ml.

0.25 ml of enzyme solution was mixed with 1.75 ml of the substrate solution (1.5% w/v) at 50° C. and the reaction was stopped after 10 min by addition of DNS solution. Followed by heating to 95° C. for 5 minutes.

The optical density was measured at 540 nm ($OD_{540\ nm}$) of the different samples.

Calculation

The enzyme activity is determined from the standard curve as shown in FIG. 2.

The activity is calculated as follows:

$$\text{Activity}\ (u \cdot ml^{-1}\ \text{or}\ u \cdot g^{-1}) = \frac{T-c}{m} \times A \times \frac{1}{180.16} \times 10^3 \times \frac{1}{V} \times \frac{1}{t} \times D$$

where:

$T = \Delta OD_{540nm}\ \text{TEST}$ $= OD_{540nm}\ \text{TEST} - OD_{540nm}\ \text{BLANK}$ m=gradient of the standard curve (approximately 1.0)
c=y axis intercept of the standard curve (always negative and approximately −0.02)
180.16=molecular weight of glucose
$10^3$=to convert to μmoles
A=assay volume in ml
V=enzyme volume in ml
t=assay time in minutes
D=actual enzyme dilution factor (e.g. for 1.000 g diluted to 1 liter D=1000)

Assay 10. Laminarinase (DNS Laminarin Method)

Principle

The reaction, catalysed by laminarinase, involves the endohydrolysis of 1,3-glucosidic bonds in 1,3-β-D-glucans. Substrates include laminarin, paramylon and pachyman. The products of the reaction (β-1,3-glucan oligosaccharides) are determined colourimetrically by measuring the resulting increase in reducing groups using a 3,5-dinitrosalicylic acid reagent. Enzyme activity is calculated from the relationship between the concentration of reducing groups, as glucose equivalents, and absorbance at 540 nm.

The assay was carried out at pH 5.0 and 50° C., but it can be performed at different values of pH and temperature for the additional characterisation and specification of enzymes.

Unit Definition

One unit of laminarinase activity is defined as the amount of enzyme which produces 1 μmole glucose equivalents per minute under the conditions of the assay (pH 5.0 and 50° C. (or as specified)).

Materials

See materials given above for the Cellulase activity assay.

Laminarin (from *Laminaria digitata*). Supplier: Sigma-Aldrich Co. Ltd. Product no.: L 9634

1.00%(w/v) solution) Laminarin solution (substrate solution 0.1M sodium acetate buffer, pH 5.0)

1.75 ml laminarin solution is mixed with 0.25 ml diluted enzyme solution at 50° C. for 10 minutes and the reaction stopped by addition of 2 ml DNS solution.

Standard curve was made using 0, 0.125, 0.25, 0.5 and 0.75 mg/ml glucose solution.

Optical density was measured at 540 nm ($OD_{540\ nm}$).

Calculation

The activity is calculated as follows:

$$\text{Activity}\ (u \cdot ml^{-1}\ \text{or}\ u \cdot g^{-1}) = \frac{T-c}{m} \times A \times \frac{1}{180.16} \times 10^3 \times \frac{1}{V} \times \frac{1}{t} \times D$$

where:
$= OD_{540nm}\ \text{TEST} - OD_{540nm}\ \text{BLANK}$ $T = \Delta OD_{540nm}\ \text{TEST}$ m=gradient of the standard curve (approximately 1.0)

c=y axis intercept of the standard curve (always negative and approximately −0.03)

180.16=molecular weight of glucose $10^3$=to convert to μmoles

A=assay volume in ml (2.00 ml used in example 5)

V=enzyme volume in ml (0.25 ml used in example 5)

t=assay time in minutes (10 minutes used in example 5)

D=enzyme dilution factor (e.g. for 1 g diluted to 1 liter D=1000)

Assay 11. Endo-1,4-β-xylanase (DNS Birchwood Xylan Method)

Principle

The reaction, catalysed by endo-1,4-β-xylanase, involves the endohydrolysis of the 1,4-β-D-xylosidic bonds in xylan (e.g. birchwood xylan or cereal substituted xylans such as wheat arabinoxylan) forming β-1,4 xylan oligosaccharides.

The products of the reaction (β-1,4-xylan oligosaccharides) was determined colorimetrically by measuring the resulting increase in reducing groups using a 3,5-dinitrosalicylic acid reagent. Enzyme activity is calculated from the relationship between the concentration of reducing groups, as xylose equivalents, and absorbance at 540 nm.

The standard assay was carried out at pH 3.5, but it can be performed at different pH values for the additional characterisation and specification of enzymes.

Unit Definition

One unit of endo-1,4-β-xylanase activity is defined as the amount of enzyme which produces 1 μmole xylose equivalents per minute under the conditions of the assay (pH 3.5 (or as specified) and 50° C.).

Materials:

See the list of materials given above for the Cellulase activity assay.

Birchwood xylan. Supplier: Sigma Chemical Co. Product no.: X 0502

D(+)-Xylose 'AnalaR'. Supplier: Merck Ltd (BDH). Product no.: 10372 M.W.: 150.13

1.5%(w/v solution) Birchwood xylan solution in 0.1 sodium acetate buffer, pH 4.0 (substrate solution)

Xylose standard solution (0.50 mg/ml)

Procedure 1.75 ml birchwood xylan solution was mixed with 0.25 ml diluted enzyme solution at 50° C. for 10 minutes, the reaction was stopped by addition of 2 ml DNS solution, followed by heating to 95° C. for 5 minutes. Optical density was measured at at 540 nm ($OD_{540\ nm}$).

Figure 3:
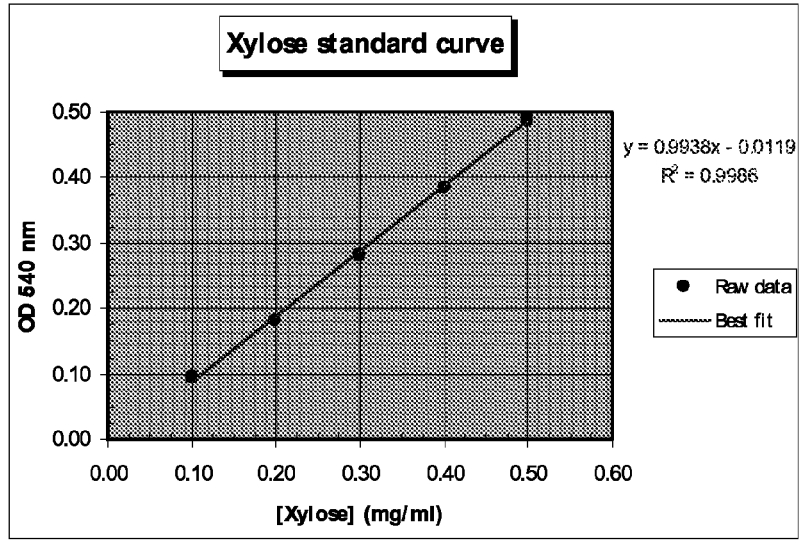
FIG. 3 shows a xylose standard curve made as described in "Assay 11" in the following under the heading "Assays".

A standard curve was made from 0.125, 0.250, 0.375, 0.500 mg/ml xylose (see FIG. 3)

Calculation

The activity is calculated as follows:

$$\text{Activity}\ (u \cdot ml^{-1}\ \text{or}\ u \cdot g^{-1}) = \frac{T - c}{m} \times A \times \frac{1}{150.13} \times 10^3 \times \frac{1}{V} \times \frac{1}{t} \times D$$

where:

$= OD_{540nm}\ \text{TEST} - OD_{540nm}\ \text{BLANK}$ $T = \Delta OD_{540nm}\ \text{TEST}$ m=gradient of the standard curve (approximately 1.0)

c=y axis intercept of the standard curve (always negative and approximately −0.02)

150.13=molecular weight of xylose $10^3$=to convert to μmoles

A=assay volume in ml (2.00 ml used in example 5)

V=enzyme volume in ml (0.25 ml used in example 5)

t=assay time in minutes (10 minutes used in example 5)

D=actual enzyme dilution factor (e.g. for 1.000 g diluted to 1 liter D=1000)

Assay 12. α-Amylase (fungal) (Ceralpha Method for Fungal α-amylase using Amylase HR Reagent)

Principle

The assay of α-amylase is carried out using Megazyme's Ceralpha method for fungal α-amylases using Amylase HR reagent (CER 07/00, ICC Standard no. 303). The assay is based on the enzymatic hydrolysis of the defined oligosaccharide "non-reducing-end blocked p-nitrophenyl maltoheptaoside" (BPNPG7) in the presence of excess levels of thermostable α-glucosidase. The assay was carried out at pH 5.4. However, the assay can be performed at different pH values for assay of different α-amylases and the additional characterisation and specification of enzymes. A feature of the Amylase HR reagent is the incorporation of the thermostable α-glucosidase which means that the assay can be carried out over a broader range of pH values (pH 5.2-7.0) and at temperatures up to 60° C.

Unit Definition

One unit of α-amylase activity, termed a Ceralpha unit, is defined as the amount of enzyme, in the presence of excess thermostable α-glucosidase which produces 1 μmole p-nitrophenol from BPNPG7 per minute under the conditions of the assay (pH 5.4 (or as specified) and 40° C.).

Materials

Amylase HR (high range) assay reagent. Supplier: Megazyme International Ireland Ltd. Product no.: R-AMHR4

DL-Malic acid (DL-Hydroxybutanedioic acid). Supplier: Sigma-Aldrich Company Ltd. Product no.: M 0875. M.W.: 134.09

Sodium hydroxide pellets 'AnalaR'. Supplier: Merck Ltd (BDH). Product no.: 10252. M.W.: 40.00

Sodium chloride 'AnalaR'. Supplier: Merck Ltd (BDH). Product no.: 10241. M.W.: 58.44

Calcium chloride 2-hydrate 'AnalaR' (calcium chloride dihydrate). Supplier: Merck Ltd (BDH). Product no.: 10070. M.W.: 147.02 tri-Sodium orthophosphate 'AnalaR' (tri-Sodium orthophosphate dodecahydrate). Supplier: Merck Ltd (BDH). Product no.: 10384. M.W.: 380.12 p-Nitrophenol (10 μmoles/ml solution) (4-Nitrophenol). Supplier: Sigma-Aldrich Company Ltd. Product no.: 104-1

Substrate solution (Amylase HR reagent) was made by dissolving one Amylase HR reagent vial in 10.0 ml glass distilled water.

1M and 0.05 M Malic acid buffer, pH 5.4

Stopping reagent (1%(w/v solution) tri-sodium orthophosphate (anhydrous) solution)

50 μM p-Nitrophenol standard in 1% (w/v solution) tri-sodium orthophosphate (anhydrous) solution, pH 11.0, made by dilution of p-nitrophenol solution (10 μmoles/ml solution) 200 fold in 1% (w/v solution) tri-sodium orthophosphate (anhydrous) solution, pH 11.0.

Preparation of Diluted Enzyme Solutions

Megazyme recommend that all enzyme solutions are prepared minimal initial 50 fold dilution (e.g. 1 ml/g made up to 50 ml) with 0.05M malic acid buffer, pH 5.4. Subsequent dilutions are made with 0.05M malic acid buffer, pH 5.4 until a dilution suitable for assay is obtained.

Procedure

The spectrophotometer being used should be standardised with the 50 µM p-nitrophenol standard in 1% (w/v solution) tri-sodium orthophosphate (anhydrous) solution, pH 11.0. This solution should give an optical density at 400 nm (OD400 nm)=0.905 (as EM of p-nitrophenol at 400 nm in 1% (w/v solution) tri-sodium orthophosphate (anhydrous) solution, pH 11.0=18.1×103).

0.10 ml substrate solution (Amylase HR reagent) was mixed with 0.10 ml diluted test enzyme solution at 40° C. for 10 minutes the reaction was stopped by addition of 1.50 ml Stopping reagent (1%(w/v solution) tri-sodium orthophosphate (anhydrous) solution). Optical density was measured at 400 nm ($OD_{400\ nm}$)

Calculation

The activity is calculated as follows:

$$\text{Activity } (u \cdot ml^{-1} \text{ or } u \cdot g^{-1}) = T \times A \times \frac{1}{V} \times \frac{1}{18.1} \times \frac{1}{t} \times D$$

where:

$$T = \Delta OD_{400nm} \text{ TEST}$$
$$= OD_{400nm} \text{ TEST} - OD_{400nm} \text{ BLANK}$$

18.1=EmM of p-nitrophenol at 400 nm in 1%(w/v solution) tri-sodium orthophosphate (anhydrous) solution, pH 11.0=18.1

A=total assay volume in ml
(1.70 ml used in example 3)
V=enzyme volume in ml
(0.10 ml used in example 3)
t=assay time in minutes
(10 minutes used in example 3)
D=total enzyme dilution factor (e.g. for 1 g diluted to 1 liter: D=1000)

Assay 13, Alpha-Holoamylase Enzyme Activity

Principle

An enzyme sample is allowed to react with a standard starch solution under specified conditions. The amount of alpha-holoamylase activity is measured by the rate at which the iodine-staining capacity of the starch is decreased.

Materials:
Sodium Hydroxide Solution, 10% (w/v)
Buffer Solution, pH 3.8 (143 ml/L of glacial acetic acid (99.7% CH$_3$COOH, S.G=1.05). Adjusted to pH 3.8 using 10% sodium hydroxide solution.
Acetic Acid, 5.0 M
Iodine, 5.00% and 0.1% solution
Starch Substrate Solution, 1.25%

Procedure:

The enzyme product was diluted. The dilution used in the assay should contain 0.02-0.1 units/ml.

9.9 ml of a 0.003% iodine solution was mixed with 4.0 ml aliquot of starch substrate solution at 60° C. in water for 10 minutes. 1 ml aliquot of deionized water is added and after 10 min absorbance was measured at 650 nm after adjusting the spectrophotometer to zero with water.

Calculations $$\text{Activity} = \log\left(\frac{\text{Average Blank absorbance}}{\text{Sample absorbance}}\right) \times \left(\frac{\text{Dilution volume}}{\text{Sample size}}\right) \times 0.245$$

Activity is in u/g or u/ml depending whether the sample size is in g or ml.

Assay 14: Glucoamylase Activity (GAU)

This assay is based on the ability of glucoamylase to catalyse the hydrolysis of p-nitrophenyl-alpha-D-glucopyranoside (PNPG) to glucose and p-nitrophenol. At an alkaline pH the nitrophenol forms a yellow colour that is proportional to glucoamylase activity and is monitored at 400 nm via the use of an enzyme standard.

Reagents required:
0.1M Sodium acetate buffer with pH 4.3
0.1M Borax solution
1.1 mg/ml PNPG substrate (Sigma N1377)

Standard preparation is made from a lot of glucoamylase with a known activity in GAU. The standard enzyme is diluted using sodium acetate buffer (0.1M) so that its net absorbance falls within the linear range of the assay.

Procedure:

250 µl acetate buffer is mixed with 200 µl of the enzyme sample, 500 µl substrate solution is added, and $A_{400}$ measured after 10 min at 30° C.

Activity is determined by the correlation of absorbance and GAU as determined by the standard curve.

Assay 15. Determination of Protein

Total protein is determined by standard assays using either the BCA™ protein Assay Kit #23225 provided with instructions fro use from Pierce, Meridian Rd, Rockford, Ill., USA (Assay 15a) or TCA protein determination (Assay 15b) such as described below:

Total protein is determined by measuring the nitrogen content of the sample. A conversion factor of g protein/g nitrogen is used to convert the percent nitrogen content to protein. The proteins analyzed are precipitated with a 30% Trichloroacetic acid (TCA) solution, followed by reconstitution in 1N sodium hydroxide. Analysis done by a ECS 4010 Elemental Analyzer or EA 1108 Elemental Analyzer. The nitrogen content of the reconstituted samples is determined, and protein calculated based from a standard using a known protein concentration.

Assay 16. α-N-arabinofuranosidase (p-Nitrophenyl α-L-arabinofuranoside method)

Principle

The reaction, catalysed by α-N-arabinofuranosidase, involves the hydrolysis of the terminal bond, at the non-reducing α-L-arabinofuranoside residue, of α-L-arabinosides. The enzyme acts on α-L-arabinofuranosides, α-L-arabinans containing (1,3)- and/or (1,5)-linkages, arabinoxylans and arabinogalactans.

The assay of α-N-arabinofuranosidase is based upon the enzymatic hydrolysis of p-nitrophenyl α-L-arabinofuranoside. The assay is a "two-point", rather than a "continuous monitoring", method. The calculation of enzyme activity is based on measurements taken only at the beginning and end of the incubation period. A product of the reaction, p-nitrophenol is determined colourimetrically (after pH adjustment). Enzyme activity is calculated from the relationship between the concentration of p-nitrophenol and absorbance at 400 nm.

Whilst the standard assay is carried out at pH 5.0 and 50° C., it can be performed at different values of pH and temperature for the additional characterisation and specification of enzymes. In this case only the pH of the buffer solutions (noted below) or the temperature are changed.

Unit Definition

One unit of α-N-arabinofuranosidase activity is defined as the amount of enzyme which produces 1 μmole p-nitrophenol from p-nitrophenyl α-L-arabinofuranoside per minute under the conditions of the assay (pH 5.0 and 50° C.).

Reagents Required

In all cases it is the identity and purity of the reagents, and not the supplier, which are important.

p-Nitrophenyl α-L-arabinofuranoside (Sigma-Aldrich Co. Ltd). Product no.: N 3641. M.W.: 271.2.

Sodium acetate anhydrous 'AnalaR'. Supplier: Merck Ltd (BDH). Product no.: 10236. M.W.: 82.03.

Acetic acid ("glacial") 'AnalaR'. Supplier: Merck Ltd (BDH). Product no.: 10001. M.W.: 60.05.

Glycine (ACS reagent). Supplier: Sigma-Aldrich Co. Ltd. Product no.: G 7032. M.W.: 75.07.

Sodium hydroxide solution 40% w/v. Supplier: Merck Ltd (BDH). Product no.: 19153. M.W.: 40.00.

Preparation of Reagents

The volumes of reagents given are examples. Different volumes can be prepared as required.

1. p-Nitrophenyl-α-L-arabinofuranoside Solution (Substrate Solution)

Accurately weigh 100 mg of p-nitrophenyl α-L-arabinofuranoside into a 200 ml Pyrex™ glass beaker and add 50 ml of glass distilled water. Place the beaker on the hot-plate of the heater/stirrer unit and warm gently, whilst stirring, to dissolve the p-nitrophenyl α-L-arabinofuranoside. Transfer the solution to a 100 ml volumetric flask, carefully rinse the Pyrex™ beaker with a small amount of glass distilled water and make the volume in the volumetric flask up to 100 ml with the rinsings and glass distilled water. Store this solution at 5° C. for a maximum of 4 weeks. (To store the substrate solution for longer periods aliquots of the solution can be frozen.)

2. 1M Sodium Acetate Buffer, pH 5.0 (Stock Buffer)

1M sodium acetate solution is prepared from 82.03 g anhydrous sodium acetate dissolved and made up to 1000 ml with glass distilled water. The concentration of glacial acetic acid is 17.5M. 1 M acetic acid is prepared by diluting 57.2 g, or 54.5 ml, glacial acetic acid to 1000 ml with glass distilled water. Accurately mix 70 ml 1M sodium acetate solution and 30 ml 1M acetic acid. Using a calibrated pH meter check the pH is pH 5.0. Adjust the pH if necessary.

3. 0.2M Sodium Acetate Buffer, pH 5.0 (Dilute Buffer)

Pipette 10 ml of 1M sodium acetate buffer, pH 5.0 into a 50 ml graduated volumetric flask. Make the volume up to 50 ml with glass distilled water.

4. 0.4M Glycine Solution, pH 10.8 (Stop Reagent)

Accurately weigh 6.006 g of glycine into a Pyrex™ 250 ml glass beaker and add 100 ml of glass distilled water. Place the beaker on heater/stirrer unit and stir to dissolve glycine. Using a calibrated pH meter adjust to pH 10.8 using the 40%(w/v) sodium hydroxide solution. Transfer the solution to a 200 ml glass volumetric flask and make the volume up to 200 ml with glass distilled water. The solution can be stored indefinitely at ambient temperatures.

Preparation of Diluted Enzyme Solution:

Prepare all enzyme solutions, from powder or liquid enzyme preparations, with glass distilled water. Minimise assay dilution errors by avoiding large dilution steps involving small volumes or weights. In making enzyme dilutions it is more accurate, even for a liquid sample, to weigh out the initial enzyme sample. If this is done, in the case of liquid samples it is therefore necessary to measure the specific gravity of the liquid at 20° C.

As the assay is a "two-point", rather than a "continuous monitoring", method it is important to ensure the linearity within the incubation period with different enzyme systems and conditions. Under the standard assay conditions of substrate concentration, pH, temperature and assay time the assay has been demonstrated to be linear in the range $\Delta OD_{400\,nm}$ TEST (T)=0.20-1.50. However, for good practice, the assay is operated within a defined range of $\Delta OD_{400\,nm}$ TEST (T)=0.400-0.800.

Procedure

Each enzyme sample assay involves three analyses: duplicate test (TEST) analyses and a blank (BLANK) analysis. The procedure given describes the analysis of a single enzyme sample.

1. Place three standard glass test tubes into a test tube rack. Label two of the three tubes TEST and the other tube BLANK. Make the following additions into each of the tubes:

|  | TEST | BLANK |
| --- | --- | --- |
| 0.2M Sodium acetate buffer, pH 5.0 | 1.00 ml | 1.00 ml |
| Glass distilled water | 1.00 ml | 1.00 ml |
| p-Nitrophenyl-α-L-arabinofuranoside solution | 1.00 ml | 1.00 ml |

2. Place all three tubes into the 50° C. water bath and allow to equilibrate for exactly 5 minutes.

3. Using a 250 μl fixed volume pipette, begin the assay by the addition of 0.25 ml diluted enzyme solution directly to each of the tubes labelled TEST, using a 10 second time interval, mixing the contents quickly using the vortex tube mixer and returning the tube to the 50° C. water bath.

4. After exactly 10 minutes, using the same 10 second time intervals, stop the reaction by adding and mixing, using the vortex tube mixer, 4 ml of 0.4M glycine solution, pH 10.8 (stop reagent) to each of the tubes labelled TEST.

5. Add and mix 4 ml of 0.4M glycine solution, pH 10.8 (stop reagent) to the tube labelled BLANK, followed by 0.25 ml of diluted enzyme solution. Mix using the vortex tube mixer.

6. Remove the tubes and cool in the 25° C. water bath. Measure the absorbance at 400 nm in a 1 cm glass cuvette against a water blank. Depending on the availability of a single or dual beam spectrophotometer, measurements can be made against water or against the OD400 nm BLANK. However, the advantage of making measurements against water is that it identifies any problems with the OD400 nm BLANK sample.

7. Measure the optical density at 400 nm (OD400 nm) of the different samples using a 1 cm path length glass cuvette.
   determine OD400 nm TEST for the duplicate TESTS measured;
   determine OD400 nm BLANK.

8. Repeat any TEST in which the resulting $\Delta OD_{400\,nm}$ TEST (T) is outside the range 0.400-0.800.

Calculation $$\Delta OD400 \text{ nm TEST } (T) = OD400 \text{ nm TEST} - OD400 \text{ nm BLANK}$$

$$\text{Units } (\mu mol \cdot min^{-1}) = \frac{T}{18300} \times \frac{V}{1000} \times 10^6 \times \frac{1}{t}$$

$$\text{Activity } (u \cdot ml^{-1} \text{ or } u \cdot g^{-1}) = \text{Units} \times \frac{1}{E} \times D$$

where:
T=OD$_{400\,nm}$ TEST−OD$_{400\,nm}$ BLANK
18300=Molar extinction coefficient for p-nitrophenol (1 cm path length)
V=7.25 (total liquid volume in test in ml)
1000=to convert to liters
10$^6$=to convert to μmoles
t=10 (minutes)
1 u=1 μmol·min$^{-1}$
E=0.25 (volume of diluted enzyme sample in ml)
D=Enzyme dilution factor e.g. for 1 ml diluted to 1 liter D=1000)

DEPOSIT OF BIOLOGICAL MATERIAL

The *Aspergillus tubingensis* 4 M 146 strain was deposited under the terms of the Budapest Treaty with the Centraalbureau voor Schimmelcultures, Uppsalalaan 8, NL-3584 CT Utrecht, The Netherlands/P.O. Box 85167, NL-3508 AD Utrecht, The Netherlands
and given the following accession numbers:

| Deposit Accession Number: | Date of deposit: |
|---|---|
| CBS 123488 | Sep. 30, 2008 |

The invention claimed is:

1. A process for the production of an enzyme composition, the process comprising the steps of submerged fermentation of an *Aspergillus tubingensis* strain having the deposit accession number CBS123488 in a fermentation medium, wherein said medium comprises sugar beet pulp and/or cereal bran to obtain a fermentation broth, and recovery of said enzyme composition from said fermentation medium, wherein said enzyme composition comprises
   i. endo-polygalacturonase,
   ii. exo-polygalacturonase,
   iii. pectinesterase,
   iv. pectin lyase,
   v. cellulase,
   vi. xylanase, and
   vii. arabinanase.

2. The process according to claim 1, wherein the fermentation medium comprises sugar beet pulp in the range of 1-30% w/w.

3. The process according to claim 1, wherein the fermentation medium comprises sugar beet pulp in the range of 2-8% w/w.

4. The process according to claim 1, wherein the fermentation medium comprises sugar beet pulp in the range of 3-7% w/w.

5. The process according to claim 1, wherein the sugar beet pulp has a sugar content of 0.5-20% w/w.

6. The process according to claim 1, wherein the sugar beet pulp has a sugar content of 2-8% w/w.

7. The process according to claim 1, wherein the sugar beet pulp has a sugar content of 5-40% w/w.

8. The process according to claim 1, wherein the sugar beet pulp is un-molassed.

9. The process according to claim 1, wherein the cereal bran is wheat bran.

10. The process according to claim 9, wherein the wheat bran has an arabinan content of 2-20% w/w.

11. The process according to claim 1, wherein the *Aspergillus tubingensis* strain has not been genetically modified (non-GMO).

12. The process according to claim 1, wherein the pH during the fermentation is in the range of 3-4.5.

13. The process according to claim 1, wherein the pH during the fermentation is in the range of 3-4.

14. The process according to claim 1, wherein the pH during the fermentation is in the range of 3.2-3.7.

15. The process according to claim 1, wherein the temperature during the fermentation is in the range of 25-40° C.

16. The process according to claim 1, wherein the temperature during the fermentation is in the range of 28-34° C.

17. The process according to claim 1, wherein the fermentation is conducted as an aerobic fermentation.

18. The process according to claim 1, wherein the fermentation medium further comprises ammonium sulphate and/or potassium nitrate.

19. The process according to claim 1, wherein the fermentation comprises the steps of:
   a. growing said *Aspergillus tubingensis* strain in an inoculum medium to obtain an inoculum, and
   b. adding said inoculum to said fermentation medium.

20. The process according to claim 19, wherein the inoculum medium comprises cereal bran and/or sugar beet pulp.

21. The process according to claim 19, wherein the inoculum medium comprises wheat bran.

22. An enzyme product obtainable by a process according to claim 1.

23. An enzyme product preparation comprising an enzyme product according to claim 22, and an enzyme carrier.

24. The process of claim 1, wherein said enzyme product is recovered in the form of a cell free broth from said fermentation broth.

* * * * *